United States Patent
Kopf-Sill et al.

(10) Patent No.: US 6,547,941 B2
(45) Date of Patent: Apr. 15, 2003

(54) ULTRA HIGH THROUGHPUT MICROFLUIDIC ANALYTICAL SYSTEMS AND METHODS

(75) Inventors: Anne R. Kopf-Sill, Portola Valley, CA (US); Andrea W. Chow, Los Altos, CA (US); Peter C. Jann, Santa Clara, CA (US); Morten J. Jensen, San Francisco, CA (US); Michael Spaid, Sunnyvale, CA (US); Colin B. Kennedy, Mill Valley, CA (US); Michael J. Kennedy, Los Gatos, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/920,090

(22) Filed: Jul. 31, 2001

(65) Prior Publication Data

US 2001/0045358 A1 Nov. 29, 2001

Related U.S. Application Data

(62) Division of application No. 09/536,274, filed on Mar. 27, 2000, now Pat. No. 6,358,387.

(51) Int. Cl.[7] .............................................. G01N 27/26
(52) U.S. Cl. ........................ 204/452; 204/451; 204/603
(58) Field of Search ................................ 204/451, 452, 204/453, 454, 600, 601, 603; 422/100, 68.1, 82.01

(56) References Cited

U.S. PATENT DOCUMENTS

| | | | |
|---|---|---|---|
| 3,486,805 A | 12/1969 | Kobayashi | 350/2 |
| 5,274,240 A | 12/1993 | Mathies et al. | 250/458.1 |
| 5,779,868 A | 7/1998 | Parce et al. | 204/604 |
| 5,942,443 A | 8/1999 | Parce et al. | 436/514 |
| 5,955,028 A | 9/1999 | Chow | 422/63 |
| 5,957,579 A | 9/1999 | Kopf-Sill et al. | |
| 6,001,231 A * | 12/1999 | Kopf-Sill et al. | 204/454 |
| 6,042,709 A | 4/2000 | Parce et al. | |
| 6,358,387 B1 * | 3/2002 | Kopf-Sill et al. | 204/603 |
| 6,447,727 B1 * | 9/2002 | Parce et al. | 422/100 |

* cited by examiner

Primary Examiner—Scott Kastler
(74) Attorney, Agent, or Firm—Gulshen H. Shauer; Gerald T Gray; Quine Intellectual Property Law Group, P.C.

(57) ABSTRACT

Analytical systems and methods that use a modular interface structure for providing an interface between a sample substrate and an analytical unit, where the analytical unit typically has a particular interface arrangement for implementing various analytical and control functions. Using a number of variants for each module of the modular interface structure advantageously provides cost effective and efficient ways to perform numerous tests using a particular substrate or class of substrates with a particular analytical and control systems interface arrangement. Improved optical illumination and detection system for simultaneously analyzing reactions or conditions in multiple parallel microchannels are also provided. Increased throughput and improved emissions detection is provided by the present invention by simultaneously illuminating multiple parallel microchannels at a non-normal incidence using an excitation beam including multiple excitation frequencies, and simultaneously detecting emissions from the substances in the microchannels in a direction normal to the substrate using a detection module with multiple detectors.

13 Claims, 18 Drawing Sheets

●: capillary connection region with "attached" capillary

○: unused capillary connection region

| | |
|---|---|
| 1  ● ○ ○ ○ ○ ○<br><br>○ ○ ○ ○ ○ ○ | 2  ● ○ ○ ○ ○ ○<br><br>● ○ ○ ○ ○ ○ |
| 4  ● ○ ○ ○ ● ○<br><br>● ○ ○ ○ ● ○ | 6  ● ○ ● ○ ● ○<br><br>● ○ ● ○ ● ○ |
| 8  ● ● ● ● ○ ○<br><br>● ● ● ● ○ ○ | 12  ● ● ● ● ● ●<br><br>● ● ● ● ● ● |

SIPPER PATTERNS  ◆ = suitable for 96 or 384-well
■ = suitable for 384-well only

ULTRA HIGH THROUGHPUT MICROFLUIDIC ANALYTICAL SYSTEMS AND METHODS

This Application is a divisional application of Ser. No. 09/536,274, filed on Mar. 27, 2000, now U.S. Pat. No. 6,358,387.

BACKGROUND OF THE INVENTION

The present invention relates generally to systems and methods for performing chemical and biological analyses. More particularly, the present invention relates to the design and use of an analyzer system which employs analytical substrates evaluated in a modular interface structure having one or more interchangeable modules with varying functionality for interfacing with an arrangement of analytical and control systems instruments.

Numerous systems and instruments are available for performing chemical, clinical, and environmental analyses of chemical and biological specimens. Conventional systems may employ a variety of detection devices for monitoring a chemical or physical change which is related to the composition or other characteristic of the specimen being tested. Such instruments includes spectrophotometers, fluorometers, light detectors, radioactive counters, magnetometers galvanometers, reflectometers, ultrasonic detectors, temperature detectors, pressure detectors, mephlometers, electrophoretic detectors, PCR systems, LCR systems, and the like. Such instruments are often combined with electronic support systems, such as microprocessors, timers, video displays, LCD displays, input devices, output devices, and the like, in a stand-alone analyzer. Such analyzers may be adapted to receive a sample directly but will more usually be designed to receive a sample placed on a sample-receiving substrate such as a dipstick, cuvette, analytical rotor or the like. Usually, the sample-receiving substrate will be made for a single use (i.e., will be disposable), and the analyzer will include the circuitry, optics, sample manipulation, and other structure necessary for performing the assay on the substrate. As a result, most analyzers are intended to work only with a single type of sample-receiving substrate and are not readily adaptable to be used with other substrates.

Recently, a new class of sample-receiving substrate has been developed, referred to as "microfluidic" systems. Microfluidic substrates have networks of chambers connected by channels which have mesoscale dimensions, where at least one dimension is usually between 0.1 $\mu$m and 500 $\mu$m. Such microfluidic substrates may be fabricated using photolithographic techniques similar to those used in the semi-conductor industry, and the resulting devices can be used to perform a variety of sophisticated chemical and biological analytical techniques. Microfluidic analytical technology has a number of advantages, including the ability to use very small sample sizes, typically on the order of nanoliters. The substrates may be produced at a relatively low cost, and can be formatted to perform numerous specific analytical operations, including mixing, dispensing, valving, reactions, and detections.

Another recently developed class of sample-receiving microfluidic substrates includes substrates having a capillary interface that allows compounds to be brought onto the test substrate from an external source, and which can be advantageously used in a number of assay formats for high-throughput screening applications. These assay formats include fluorogenic assays, fluorescence polarization assays, non-fluorogenic mobility shift assays, dose response assays, and calcium flux cell-based assays.

Because of the variety of analytical techniques and potentially complex sample flow patterns that may be incorporated into particular microfluidic test substrates, significant demands may be placed on the analytical units which support the test substrates. The analytical units not only have to manage the direction and timing of flow through the network of channels and reservoirs on the substrate, they may also have to provide one or more physical interactions with the samples at locations distributed around the substrate, including heating, cooling, exposure to light or other radiation, detection of light or other radiation or other emissions, measuring electrical/electrochemical signals, pH, and the like. The flow control management may also comprise a variety of interactions, including the patterned application of voltage, current, or power to the substrate (for electrokinetic flow control), or the application of pressure, vacuum, acoustic energy or other mechanical interventions for otherwise inducing flow.

It can thus be seen that a virtually infinite number of specific test formats may be incorporated into microfluidic test substrates. Because of such variety and complexity, many if not most of the test substrates will require specifically configured analyzers in order to perform a particular test. It is indeed possible that particular test substrates use more than one analyzer for performing different tests. The need to provide one dedicated analyzer for every substrate and test, however, will significantly reduce the flexibility and cost advantages of the microfluidic systems. Additionally, for a specifically configured analyzer, test substrates are generally only useful for performing a limited number of assay formats and functions. As the complexity and costs of test substrates increase, it becomes more desirable to increase the number of useful assay formats and functions for a particular test substrate-analyzer combination, or for a particular class of substrates in combination with a specifically configured analyzer.

It would therefore be desirable to provide improved analytical systems and methods that overcome or substantially mitigate at least some of the problems set forth above. In particular, it would be desirable to provide analytical systems including a modular interface structure which can support a number of different microfluidic or other test substrates having substantially different flow patterns, chemistries, and other analytical characteristics. It would also be particularly desirable to provide analytical systems including a modular substrate-to-instrument interface structure comprised of interchangeable modules to accommodate various combinations of assay formats and functions, such as different flow patterns, for a particular test substrate or a particular class of test substrates having similar design layouts and/or properties. The costs for modifying the analytical and control systems interface as well as the costs required for obtaining test substrates for desired assays would be significantly reduced.

SUMMARY OF THE INVENTION

The present invention overcomes at least some of the deficiencies described above by providing analytical systems and methods that use a modular interface structure for providing an interface between a sample substrate and an analytical unit, where the analytical unit typically has a particular interface arrangement for implementing various analytical and control functions. Using a number of variants for each module of the modular interface structure advantageously provides cost effective and efficient ways to perform numerous tests using a particular substrate or class of substrates with a particular analytical and control systems interface arrangement.

The present invention also provides an improved optical illumination and detection system for simultaneously analyzing reactions or conditions in multiple parallel microchannels. Increased throughput and improved emissions detection is provided by the present invention by simultaneously illuminating multiple parallel microchannels at a non-normal incidence using an excitation beam including multiple excitation wavelengths, and simultaneously detecting emissions from the substances in the microchannels in a direction normal to the substrate using a detection module with multiple detectors.

According to one aspect of the invention, an illumination and detection system is provided for use in illuminating a plurality of samples in a plurality of microchannels located in a detection region on a microfluidic device, and for detecting radiation emitted from the detection region, wherein the microchannels are substantially parallel along a first direction within the detection region. The system typically comprises an illumination source for providing an excitation beam having two or more excitation wavelengths, and focussing optics for focussing the excitation beam onto a first plane defined by the plurality of microchannels in the detection region such that the focussed excitation beam is elongated, having a major axis substantially perpendicular to the first direction, wherein the excitation beam impinges upon the detection region at a non-normal angle of incidence relative to the first plane, and wherein the excitation beam simultaneously excites the samples in at least two of the microchannels so as to cause the excited samples to emit radiation. The system also typically includes two or more detectors, wherein each detector detects a specific range of radiation wavelengths, and detection optics for directing radiation from the samples toward the detectors such that the wavelengths of the emitted radiation within each specific radiation wavelength range are directed toward the corresponding detector.

According to another aspect of the invention, a method is provided for simultaneously analyzing a plurality of samples in a plurality of microchannels on a microfluidic device, wherein the plurality of microchannels are substantially parallel along a first direction within a detection region on the microfluidic device. The method typically comprises the step of simultaneously exciting the samples in at least two of the microchannels in the detection region by focussing an excitation beam having two or more excitation wavelengths onto a first plane defined by the plurality of microchannels in the detection region such that the focussed excitation beam is elongated, having a major axis substantially perpendicular to the first direction, wherein the excitation beam impinges upon the detection region at a non-normal angle of incidence relative to the first plane, and wherein the excited samples emit radiation. The method also typically includes the step of simultaneously detecting the radiation emitted by the two or more excited samples using two or more detectors, wherein each of the detectors detects a specific range of radiation wavelengths. Illuminating the detection region at a non-normal incidence generally rids the detection system of any zero order reflections.

According to yet another aspect of the invention, a microfluidic device is provided, which typically comprises a fluid reservoir for holding a conducting fluid, a conducting capillary for supplying the fluid to the reservoir, wherein one end of the capillary is positioned at a first location in the reservoir, a voltage source having a first terminal and a second terminal, a first lead connecting the first terminal to the conducting capillary, and a second lead connecting the second terminal to a second location in the reservoir. In a typical operation of the microfluidic device, when the level of the fluid within the reservoir is at least at the first location, an electric current is present between the first and second terminals, and wherein when the fluid level is below the first location such that there is no contact between the fluid and the capillary, no electric current between the first and second terminals is present. The microfluidic device may also include a fluid monitoring element, such as a syringe pump, in fluid communication with the capillary. In operation, the fluid monitoring element provides fluid to the reservoir through the capillary when no electric current between the first and second terminals is present.

According to a further aspect of the invention, a method is provided for automatically refilling a fluid reservoir in a microfluidic device, wherein the device typically includes a conducting capillary and a voltage supply, wherein a first end of the capillary is typically positioned at a first level within the reservoir, wherein a first terminal of the voltage supply is typically connected to the capillary and wherein a second terminal of the voltage supply is typically connected to a location at a second level within the reservoir, the second level being below the first level. The method typically comprises the steps of detecting an absence of electric current between the first and second terminals through the capillary, wherein no electric current flows between the first and second terminals when the fluid level is below the first level in the reservoir, and automatically supplying fluid to the reservoir through the capillary using a fluid monitoring device in response to the absence of current so as to raise the fluid level within the reservoir.

According to yet a further aspect of the invention, an analytical system is provided which typically comprises a sample substrate having a plurality of substrate reservoirs and a plurality of microchannels disposed thereon, wherein the plurality of microchannels connects the plurality of substrate reservoirs, and wherein two or more of the microchannels are substantially parallel in a detection region on the substrate, and a modular interface, having two or more removably attachable interface modules, for interfacing with a plurality of instrument connectors. The modular interface typically includes a substrate interface module having at least one fluid reservoir disposed therein, wherein the substrate interface module is removably attached to the substrate, and wherein the at least one fluid reservoir is positioned so as to provide increased capacity to one of the substrate reservoirs, and an instrument interface module having a plurality of first connectors for connecting to one or more of the plurality of instrument connectors, and a plurality of second connectors for providing a connection between the instrument connectors and the substrate interface module when the substrate interface module is removably attached to the instrument interface module. The modular interface may also include other modules, such as a fluid supply module removably attached between the instrument and substrate interface modules, wherein the fluid supply module typically includes at least one fluid supply reservoir, wherein the fluid supply module also provides a connection between the substrate interface module and the second connectors of the instrument interface module.

According to still a further aspect of the invention, a microfluidic device arranged on a sample substrate is provided, which typically comprises a plurality of substrate reservoirs disposed on the substrate, and a plurality of microchannels disposed on the substrate, wherein the plurality of microchannels connects the plurality of substrate reservoirs, and wherein two or more of the microchannels are substantially parallel in a detection region on the substrate. The device also typically includes a non-linear arrangement of a plurality of sampling capillary connection regions disposed on the substrate for interfacing with one or more sampling capillaries, wherein the sampling capillary connection regions are connected to the plurality of microchannels.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 7a illustrates a capillary spacing pattern according to one embodiment which is compatible with both 96-well microtiter plate formats having up to 6 sampling capillaries and with 384-well microtiter plate formats having any number of sampling capillaries;

FIG. 7b illustrates various capillary placement patterns associated with the spacing pattern of FIG. 7a;

DESCRIPTION OF THE SPECIFIC EMBODIMENTS

Chip Design and Manufacture

Figure 1:
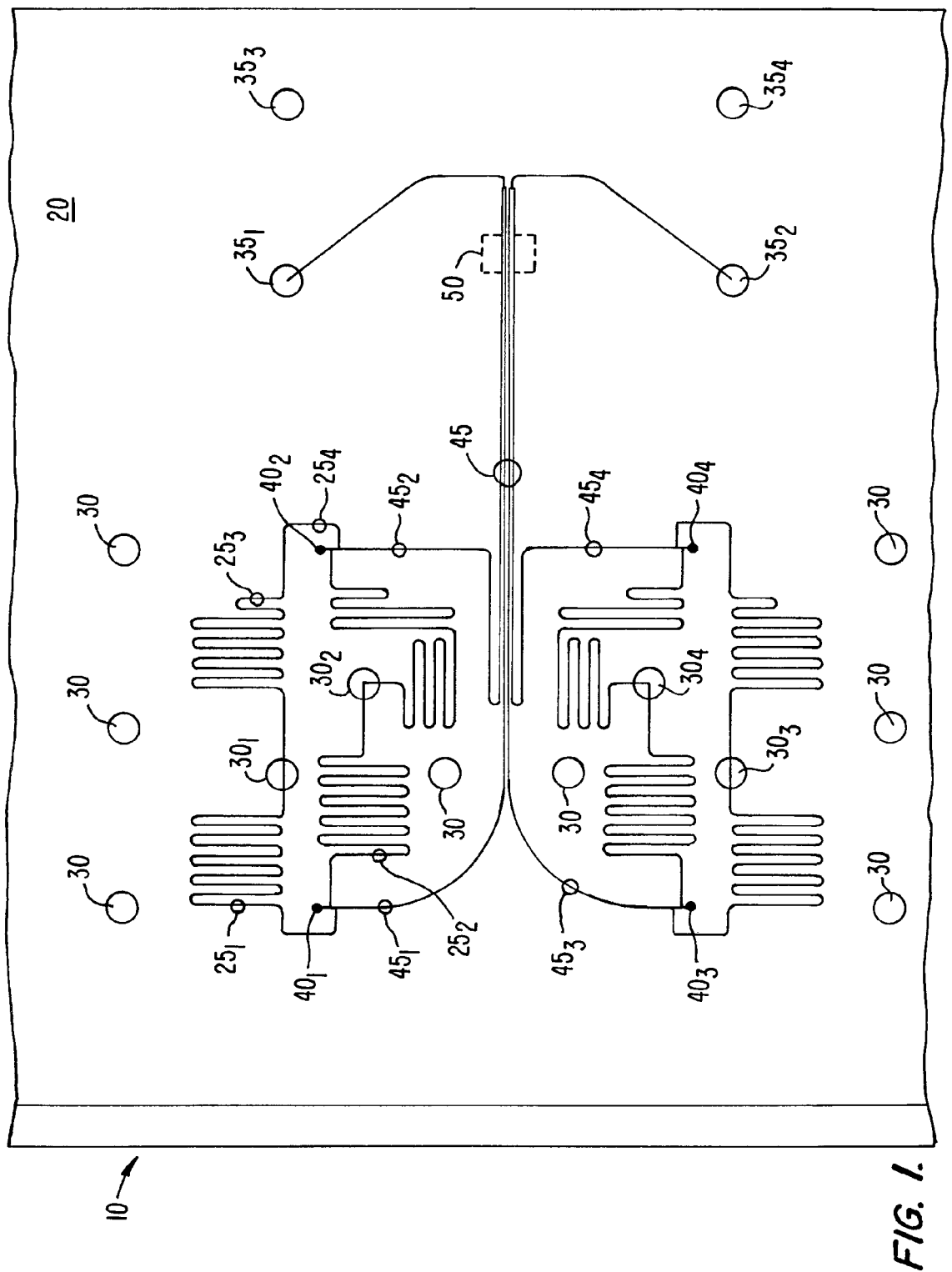
FIG. 1 illustrates an example of a microfluidic device according to an embodiment of the present invention.

FIG. 1 illustrates an example of a microfluidic device 10 according to an embodiment of the present invention. As shown, device 10 includes a body structure 20 which has an integrated network of microfluidic channels 25 disposed therein. In a preferred embodiment, device 10 includes at least two intersecting microfluidic channels to provide for various reactions, material combinations, etc. as desired. The body structure 20 also includes a plurality of reservoirs 30 disposed therein for holding reagents, sample materials and the like. The network 25 of microfluidic channels is used to connect any combination, or all, of the reservoirs 30 in any fashion as is desired by the substrate designer for the specific class of assays to be performed. Also included are waste reservoirs 35 and sampling capillary connection regions 40. Sampling capillary connection regions 40 each provide an interface with a sampling capillary that brings compounds onto device 10 from an external reservoir or reservoirs. For example, in a preferred embodiment including four capillary connection regions 40 as shown, one to four capillaries can be used to bring compounds onto device 10 from one or more external sources, such as one or more wells on a multi-well microtiter plate as is standard in the industry. In this embodiment, the capillary connection regions 40, and therefore the associated capillaries, are preferably spaced so as to be compatible with industry standard microtiter plate format spacings. A sampling capillary connection region 40 can include a reservoir interconnected with one or more of the microfluidic channels of network 25, or it can include a direct connection between the sampling capillary and one or more microfluidic channels. Examples of microfluidic devices incorporating sampling capillary elements are described in U.S. Pat. No. 5,779,868, which is incorporated herein by reference in its entirety for all purposes.

A "microfluidic" channel, or "microchannel" is a channel (sealed enclosed groove, depression, tube, capillary, etc.) which is adapted to handle small volumes of fluid. In a typical embodiment, the channel is a tube, channel or conduit having at least one subsection with at least one cross-sectional dimension of between about 0.1 $\mu$m and 500 $\mu$m, and typically less than 100 $\mu$m. Ports or reservoirs are provided in fluid communication with the channels, in order to provide fluid or other access to the interior of the channel. In operation, materials that are being analyzed, e.g., subjected to optical analysis for fluorescence emission signals, in these microscale fluidic systems, are transported along the microscale fluid channels, past a detection point, where a detectable fluorescence emission signal is measured. The signals within these channels typically result from the presence of fluorescent substances therein, e.g., fluorophores that inherently fluoresce, or are made to fluoresce, and which are used as indicators of the presence or absence of some material or condition.

Referring to FIG. 1, samples, reagents, compounds, etc. are transported from their respective reservoirs 30 and sampling capillary connection regions 40, either separately or together with other reagents, samples, compounds, etc.

from other reservoirs and sampling capillary connection regions through the network 25 of microchannels into a plurality of analysis channels 45, and past detection region 50 toward waste reservoirs 35. Although four microfluidic channels are shown in detection region 50, as few as one microfluidic channel, and preferably two or more, four or more, six or more, eight or more, and even twelve or more microfluidic channels can be present in detection region 50. Detection region 50 is typically transparent to allow radiation to reach the materials in the microchannels within the region and/or to allow emitted or detected radiation to leave the region. Detection region 50, in one embodiment is comprised of a transparent region of body structure 20, but may be a separate transparent window fabricated into body structure 20. Typically, the body structure 20 is itself fabricated from a transparent material, such as glass or transparent polymers, thereby obviating the need for a separate transparent region to define the detection window.

In an exemplary application, the microfluidic device 10 shown in FIG. 1 is used to perform high throughput assay operations, screening multiple samples or compounds against one to more different reagent systems, e.g., biochemical system components. Examples of microfluidic high throughput screening assays and systems are described in commonly owned U.S. Pat. No. 5,942,443, which is incorporated herein by reference.

Briefly, reagents that are used in the particular screening assay, e.g., an enzyme and substrate, specific binding reagents, e.g., receptor ligand pairs, complementary pairs of nucleic acids, etc., cells which encompass more complex biochemical systems, are placed into the appropriate reservoirs of the device 10. For example, in the case of paired reagents, e.g., and enzyme and its substrate, the enzyme solution is placed into, e.g., reservoir $30_1$, while the substrate is placed into reservoir $30_2$. By applying a constant vacuum at reservoir $35_1$, the enzyme and substrate begin flowing from the reservoir through channels $25_1$ and $25_2$, respectively, and into analysis channel $45_1$. Concurrently, the applied pressure differential draws plugs of sample materials into the analysis channel through the capillary connection region $40_1$. Specifically, a capillary element having a capillary channel disposed therethrough (not shown) is provided attached to the device and in fluid communication with the capillary connection region $40_1$ of the device. The open end of the capillary channel is then contacted with sources of sample material, drawing in a small aliquot of the material and transporting that aliquot as a plug into the analysis channel.

Within analysis channel $45_1$, the enzyme and substrate mix together to form a reaction mixture which flows along analysis channel $45_1$ past detection region 50. There, the results of the reaction between the enzyme and substrate are measured. Barring any outside influence, e.g., change in environment, flow rate, etc., the signal detected at the detection region 50 is at a constant level, reflecting the enzymatic reaction that takes place while the reaction mixture flows along analysis channel $45_1$. Periodically, the sample material plugs are introduced into the analysis channel $45_1$ via the capillary connection region $40_1$. Where the sample material has an effect on the reaction that is occurring, it will result in a change in the steady state signal observed at the detection zone 50.

As can be seen in FIG. 1, the reagent reservoirs $30_1$ and $30_2$, which contained the enzyme and substrate in the present example, are also fluidly connected to another analysis channel $45_2$ via channels $25_3$ and $25_4$, respectively. Thus, while a screening assay is being carried out in analysis channel $45_1$, a parallel screening assay can be carried out in analysis channel $45_2$. Because analysis channel $45_2$ is coupled to a different capillary element via capillary connection region $40_2$, it can sample from different sources of sample material than the other capillary elements. As shown, the capillary elements are positioned to sample from different wells on a multiwell plate, e.g., 96 well, 384 well or 1536 well. The channels, reservoirs and capillary elements on the opposite side of the device 10 perform similar functions, while sampling from still different sources of sample material.

In the device shown, the reagents from each of the various reservoirs and the capillary elements are transported at equivalent rates among the various different analytical modules. This is generally accomplished by providing channel layouts for each module that are equivalent to the other modules in terms of flow resistance. Accordingly, when a constant vacuum is applied at reservoirs $35_1$ and $35_2$, the flow rates of reagents into and through each of the four analysis channels $45_{1-4}$ is equivalent, allowing direct comparison of results from one channel versus another channel.

Figure 2:
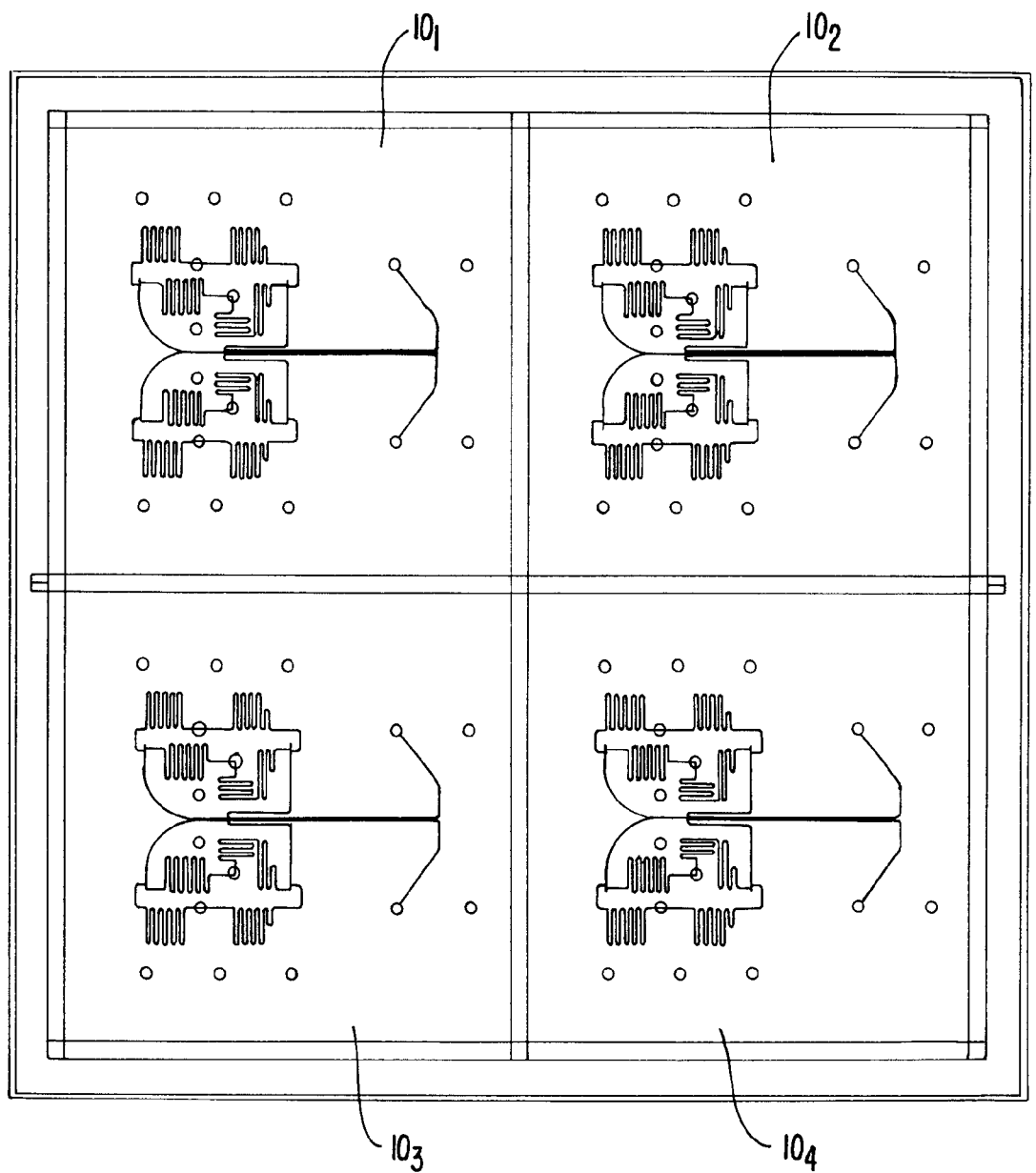
FIG. 2 illustrates an example of a wafer mask for use in fabricating four microfluidic devices similar to the microfluidic device shown in FIG. 1 using photolithographic techniques.

In one embodiment, microfluidic devices such as device 10 are fabricated using photolithographic techniques similar to those used in the semiconductor industry. FIG. 2 illustrates an example of a wafer mask for use in fabricating four microfluidic devices $10_{1-4}$ similar to microfluidic device 10 of FIG. 1 using such techniques. A four chip mask pattern such as that shown in FIG. 2 is optimal for use with a standard 5" square wafer (e.g., glass or quartz) with chips having 57×57 mm dimensions.

Modular Interface

The present invention is particularly useful for a number of assay formats for high-throughput screening applications, including, for example, fluorogenic assays, fluorescence polarization assays, non-fluorogenic mobility shift assays, dose response assays, and a variety of cell-based assays including, e.g., calcium flux based assays, viability assays, etc. For increased throughput, these assay formats and compound accession modes can be operated in multiple sampling capillary formats, using anywhere from one to twelve or more parallel channels within the device, and one, two, four, six, eight, or twelve or more discrete sampling capillary elements. Many of the designs for these formats will generally require different numbers of reagent wells and a different interface with vacuum, electrode, and temperature controls from the instrument array. To avoid needing a different interface for each chip design, a modular substrate-to-instrument, or chip-to-instrument, interface in discrete layers is provided to accommodate various combinations of assay formats and functions using a number of variants for each layer. One embodiment of a modular interface structure according to the present invention is illustrated schematically in FIG. 3. According to the embodiment, a modular chip-to-instrument interface structure for interfacing an array of instruments with a substrate is provided in two or more discrete layers. For example, according to the embodiment shown in FIG. 3, a chip-to-instrument interface structure is provided in four discrete layers: the adapter layer 110, the fluid supply layer 130, the holder layer 120 and the heater block layer 160.

In a preferred embodiment, each modular interface layer is embodied in a separate module, each having an array of one or more interface connectors, or components, for interfacing with connectors of other modules, the substrate and/or the analytical and control instrument array. As used herein, the phrase "interface component," or "interface connector," refers to any one of a variety of discrete components or regions present in the interface arrays of the various interface modules, the instrument array 150 and the sample substrate 140. Interface components, or connectors, will generally provide for electrical or other energy transfer, analog or digital signal transfer, fluid transfer, heat transfer, pressure and vacuum transfer, energy transmission such as the transmission of light or other radiation, energy emission detection and the like.

Adapter layer 110 generally provides an interface to the array of analytical and control instrument connectors (the "instrument array") of the instrument layer 150. Adapter layer 110 also provides an interface to the next interface layer with any desired configuration of interface connectors (e.g., any specific configuration of electrodes, pressure and vacuum ports, and temperature control regions) as are needed for the desired assay format and/or selected substrate layout. Holder layer 120 provides an interface to the array of connectors present on the sample substrate with any desired configuration of interface connectors as are needed for the desired assay format and/or selected substrate layout. Holder layer 120, in one embodiment, is comprised of a plastic material, or other composite material. Holder layer 120, in one embodiment also provides capacity for reagent and buffer reservoirs, or wells 125, and provides electrical insulation to prevent surface conduction between wells. Holder layer 120 in some embodiments may serve as a three dimensional fluid distribution system for reagents and buffers.

Figure 3:
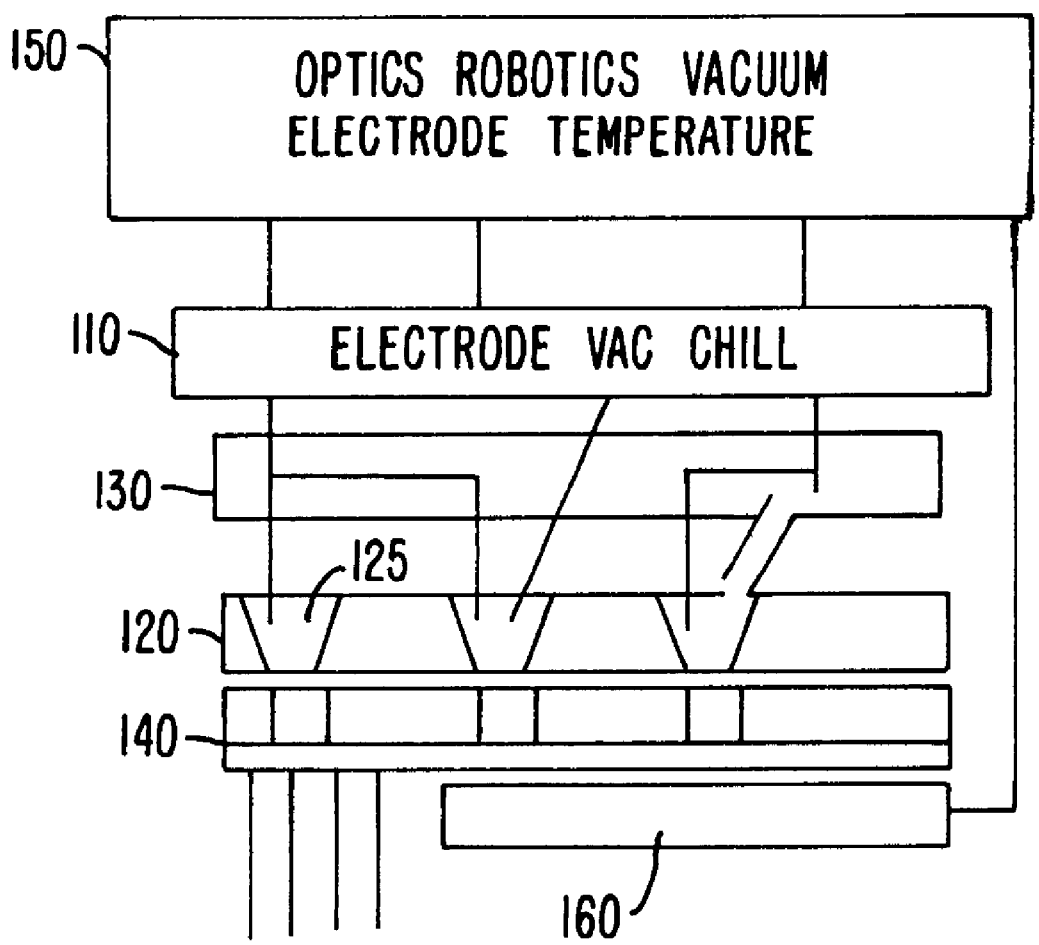
FIG. 3 is a block diagram that illustrates a modular substrate-to-instrument interface structure according to an embodiment of the present invention.

Fluid supply layer 130 is optionally provided for those chips where the volume of buffer required is larger than that defined by holder layer 120. For example, the use of fluid supply layer 130 is advantageous for chips having the DMSO sipping/dilution function when the volume of buffer required is larger than that defined by holder layer 120 under extended operating times. In one embodiment, the buffer feed rate from fluid supply layer 130 to the wells on holder layer 120 can be controlled using electrical conductivity detection techniques as described in more detail below. Fluid supply layer 130 also provides any desired configuration of interface connectors for interfacing with adjacent layers (e.g., adapter layer 110 and holder layer 120 as shown in FIG. 3) as are needed for the desired assay format and/or selected substrate layout.

Heater block layer 160 is optionally provided for heating and cooling fluid wells and reservoirs and reaction channels as will be described in more detail later.

A particular advantage of the present invention is that each layer, or module, of the interface structure can be configured to interface with any one of a variety of connector configurations provided by each adjacent interface array (e.g., the interface array of an adjacent module, the substrate, or the instrument array) as is desired to perform the desired assay. For example, for a specific array of instrument connectors, adapter layer 110 can be configured to interface with any or all connectors of the instrument array 150, and likewise can be configured to provide an array of connectors to the next layer, e.g., fluid layer 130, when used, or holder layer 120. The array of connectors provided by adapter layer 10 may include all, or a subset, or a superset, of the functionality provided by the instrument array 150. For example, adapter layer 110 may interface with one electrode connector and one vacuum connector of the instrument interface array 150, but it may be configured to provide only one electrode connector and no vacuum connector to the next layer (i.e., subset), or it may be configured to supply two electrode connectors and two vacuum connectors to the next layer (i.e., superset). Likewise, when used, fluid supply layer 130 can be configured to interface with any or all connectors provided by adapter layer 110, and likewise can be configured to provide an array of connectors to the next layer, e.g., holder layer 120. The array of connectors provided by fluid layer 130 may include all or a subset of the functionality provided to fluid layer 130 by adapter layer 110. Similarly, holder layer 120 can be configured to interface with any or all connectors provided by it's adjacent layer, e.g., fluid layer 130 or adapter layer 110, and likewise can be configured to provide an array of connectors to the sample substrate 140. The array of connectors provided by holder layer 120 may include all, or a subset, or a superset, of the functionality provided to holder layer 120.

In this manner, the designer of the sample substrate is free to optimize the size, flow paths, and other features of the sample substrate without undue regard to the nature of the instrument array or the interface structure. Likewise, the designer of the analytical and control instruments is free to optimize the connectivity and functionality, and other features of the instruments without undue regard to the nature of the sample substrate or the interface structure. Within a wide latitude, most specific design features of a sample substrate and a specific instrument array may be accommodated by appropriately designing the various layers of the modular interface structure. It will therefore be appreciated that the system architecture using the modular interface structure as an interface between the sample substrate and an instrument array provides for significant design flexibility.

Electrical connections, both for power and signal transfer, will generally include conventional connectors in the form of electrodes, pins, plugs, zero insertion force (ZIF) connectors, and the like. Such electrical connections will usually require mating connectors in the interface modules which are brought together when the system is put together. The electrical connectors will often be present on a surface or edge of an interface module so that corresponding components will be engaged against each other when the modules are removably attached to each other and to the substrate. Similarly, surface or edge electrodes in the substrate interface module, e.g., holder module 120, may be provided to mate with corresponding surface or edge electrodes on the sample substrate. The electrodes on the sample substrate may then be connected internally in the substrate to the desired reservoirs or fluid flow channels in order to effect electrokinetic flow control. In other cases, however, it will be desirable to provide interface components in the sample substrate interface module, e.g., holder module 120, which directly contact the fluid to be electrokinetically controlled. For example, probes or pins may be provided which will penetrate into open wells or through septums on the sample substrate in order to permit direct contact and application of electrical potential when modules are removably attached. In an embodiment where wells on holder module 120 are in fluid communication with wells on the sample substrate for the purpose of providing extra capacity to the substrate wells, it may be desirable to provide interface components in the adapter module 110, or in fluid module 130 when used, which directly contact the fluid in the wells of holder module 120. For example, capillaries or other connectors that provide fluid communication, may be provided which will penetrate into open wells or through septums on the sample substrate and/or the holder module in order to permit direct contact and application of electrical potential when modules are removably attached.

A particular class of interface components employed by the analytical systems of the present invention are referred to as "flow biasing connectors." Flow biasing connectors are intended to identify those interface components which can effect fluid flow in sample substrates, particularly on microfluidic substrates having a network of flow channels and reservoirs. For microfluidic substrates employing electrokinetic flow management, the flow biasing connectors on the interface modules will typically include electrodes, probes, pins, or the like distributed within, or on, each module to mate with any reservoirs on the modules and with the network of flow channels and reservoirs in the sample substrate as generally described above. The electrodes will usually have corresponding electrode terminals present on the sample substrate so that the electrode terminals may be interconnected to corresponding electrical connectors on the sample substrate interface. In other cases, as described above, the flow biasing connectors may be probes or pins which are positioned to directly engage fluids present on or in the sample substrate or the holder module. For example, an array of pins may be provided on the adapter module 110, or the fluid module 130 when used, such that when removably attached to holder module 120, the pins penetrate into open sample wells 125 on the holder module 120. The wells on the sample substrate 140 and the wells 125 on the holder module 120, of course, need not be open and could be covered with any penetrable membrane or septum which is pierced by the pins or fluid connectors, such as capillaries, when the cover is closed. Other flow biasing connectors include acoustic energy sources (e.g., piezoelectric transducers) positioned within the sample substrate interface module so that they engage the sample substrate 140 and/or holder module 120 at positions intended to induce fluid flow through the flow channels. In preferred aspects, however, material movement through the channel networks is governed by applied pressure differentials. Typically this involves application of a negative and/or positive pressure to one or more of the reservoirs of the device to draw or force material through channels connected to those reservoirs. Thus, in such cases, the flow biasing connectors represent pressure or vacuum sources coupled to one or more reservoirs of the device. As noted previously, negative pressure applied at a common waste reservoir (e.g., reservoir $35_1$ of FIG. 1) is used to draw material into and through the channels of the device. Further, by appropriately configuring the interconnected channels coupled to the particular waste reservoir, one can accurately regulate the relative flow rates of materials in the various interconnected channels, e.g., by varying the channel resistances. In alternative aspects, multiple positive pressure sources are coupled to the various reagent supply reservoirs (e.g., reservoirs $30_1$ and $30_2$)to drive material flow through the channels of the device, which may be used alone or in combination with an applied vacuum at the waste reservoir, e.g., to ensure the drawing of sample materials into the capillary element.

Figure 4A:
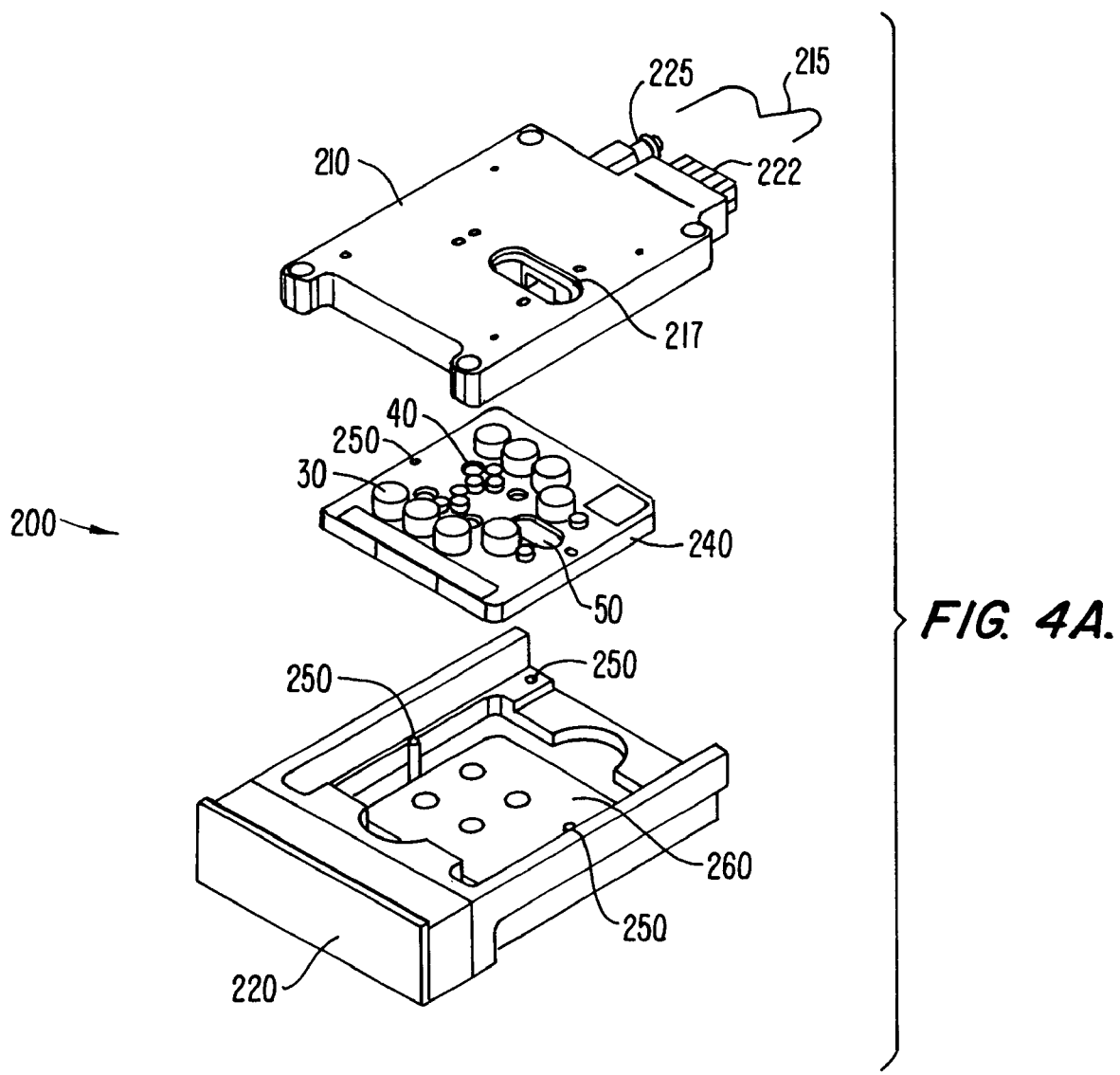
FIGS. 4a–d illustrate various isometric and side views of an exemplary modular interface structure according to an embodiment of the present invention.

FIG. 4a illustrates an isometric view of an exemplary modular interface structure 200 according to an embodiment of the present invention. As shown in an "unattached" state in FIG. 4a, interface structure 200 according to this embodiment includes holder module 220, adapter module 210 and sample substrate 240. Holder module 220 is provided as a structure for holding the modular interface structure. For example, one or more of the interface modules can be provided with locating pins or holes for mating with locating holes or pins 250 of holder 220. Alternately, adapter module 210, or any other module, may act as a holding or support structure. In such an embodiment, the module(s) providing structural support is provided with one or more locating pins and/or holes to mate with one or more pins and/or locating holes on the other modules.

Figure 5A:
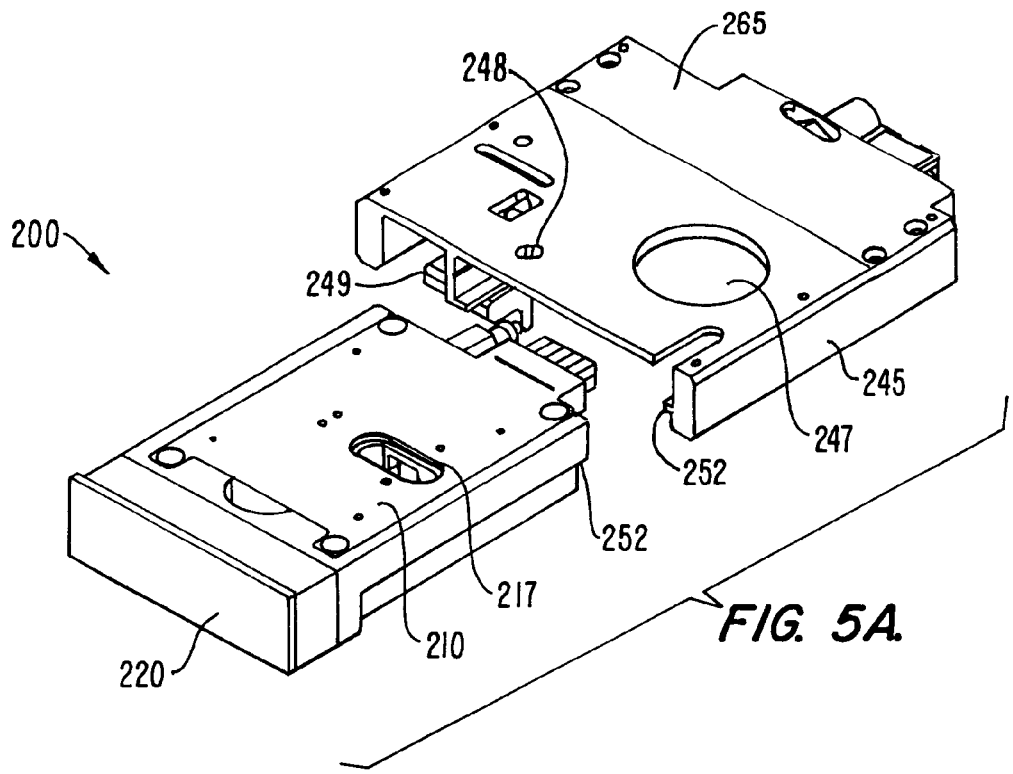
FIGS. 5a–b illustrate isometric views (top and sides) of the exemplary modular interface structure of FIGS. 4a–d according to an embodiment of the present invention.

As shown in FIG. 4a, adapter module 210 includes an array 215 of electrical connectors 222 for mating with an array of instrument connectors (not shown). Array 215 provides connectivity to analytical and control instruments through the array of instrument connectors (not shown). Electrical connectors 222 on array 215 includes any of a variety of electrodes, pins, plugs, zero insertion force connectors, or other types of connectors capable of effecting power and signal transfer. Also included in array 215 is a pneumatic port connector 225, such as a vacuum or pressure port, for interfacing with a vacuum or pressure source (not shown) and which connects to one or more of the parts on the substrate. Although only a specific number of connectors in a specific arrangement are illustrated in FIG. 4a, it will be apparent that any number of connectors in any configuration can be used. Additionally, adapter module 210 includes a window or opening 217 defined therein to allow radiation to pass therethrough. Sample substrate 240 as shown in FIG. 4a is a chip including fluid wells and reservoirs 30, capillary connection regions 40 and a detection region 50 (reaction channels are not shown). In one embodiment, optional heater block 260 is included for providing temperature control as will be described later. Also in one embodiment, a spring mechanism (not shown), coupled to holder 220, is provided for biasing the chip 240 toward adapter module 210 and against datum pins of the adapter plate (e.g., datum pin 248 as shown in FIG. 5a). The datum pins are provided for maintaining and controlling the z-axis position of the modules in the structure 200.

Figure 4B:
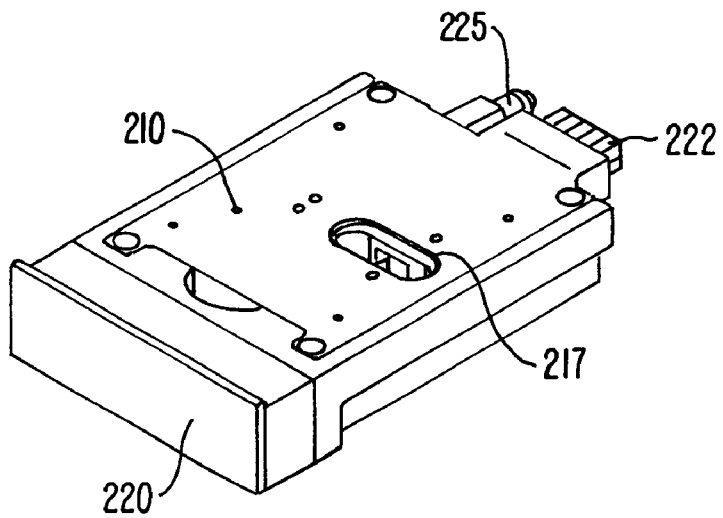

FIG. 4b illustrates an isometric view of the interface structure of FIG. 4a in an "attached" state, i.e., the modules are removably attached to each other, and the holder module 220 is removably attached to the sample substrate 240.

Figure 4C:
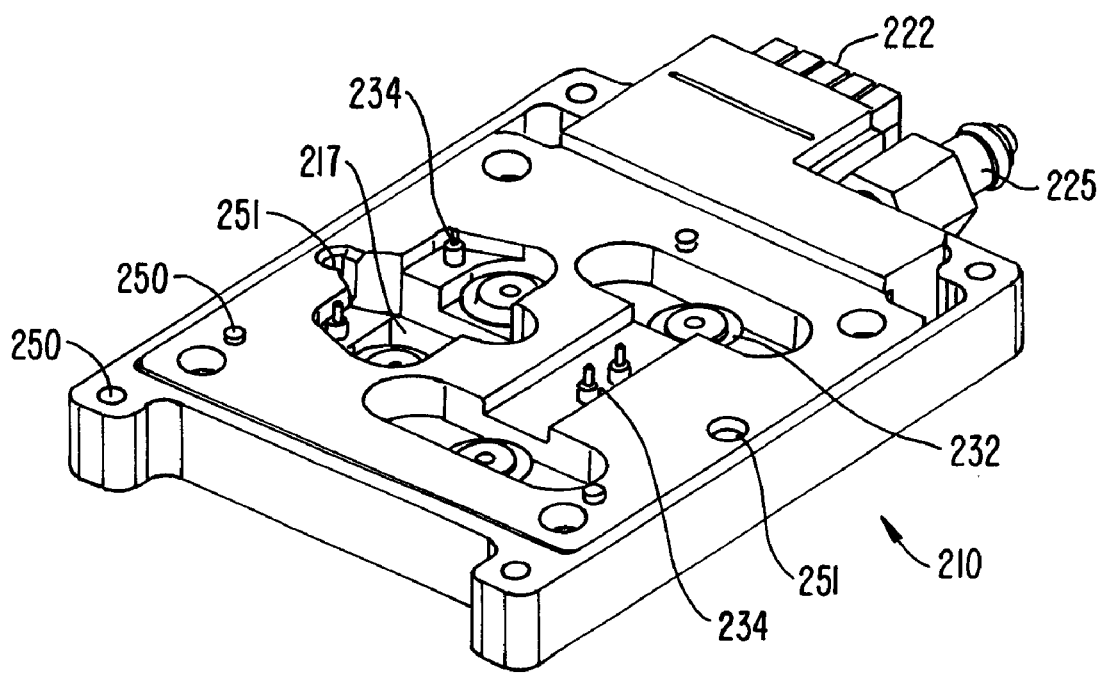

FIG. 4c illustrates the underside of an exemplary adapter module 210 according to an embodiment of the present invention. As shown, adapter module includes various connectors, such as multiple electrode pin connectors 234 and pressure seal connectors 232 (e.g., for vacuum and/or positive pressure), for interfacing with wells 30 on chip 240. Also shown are datum registration holes 251.

Figure 4D:
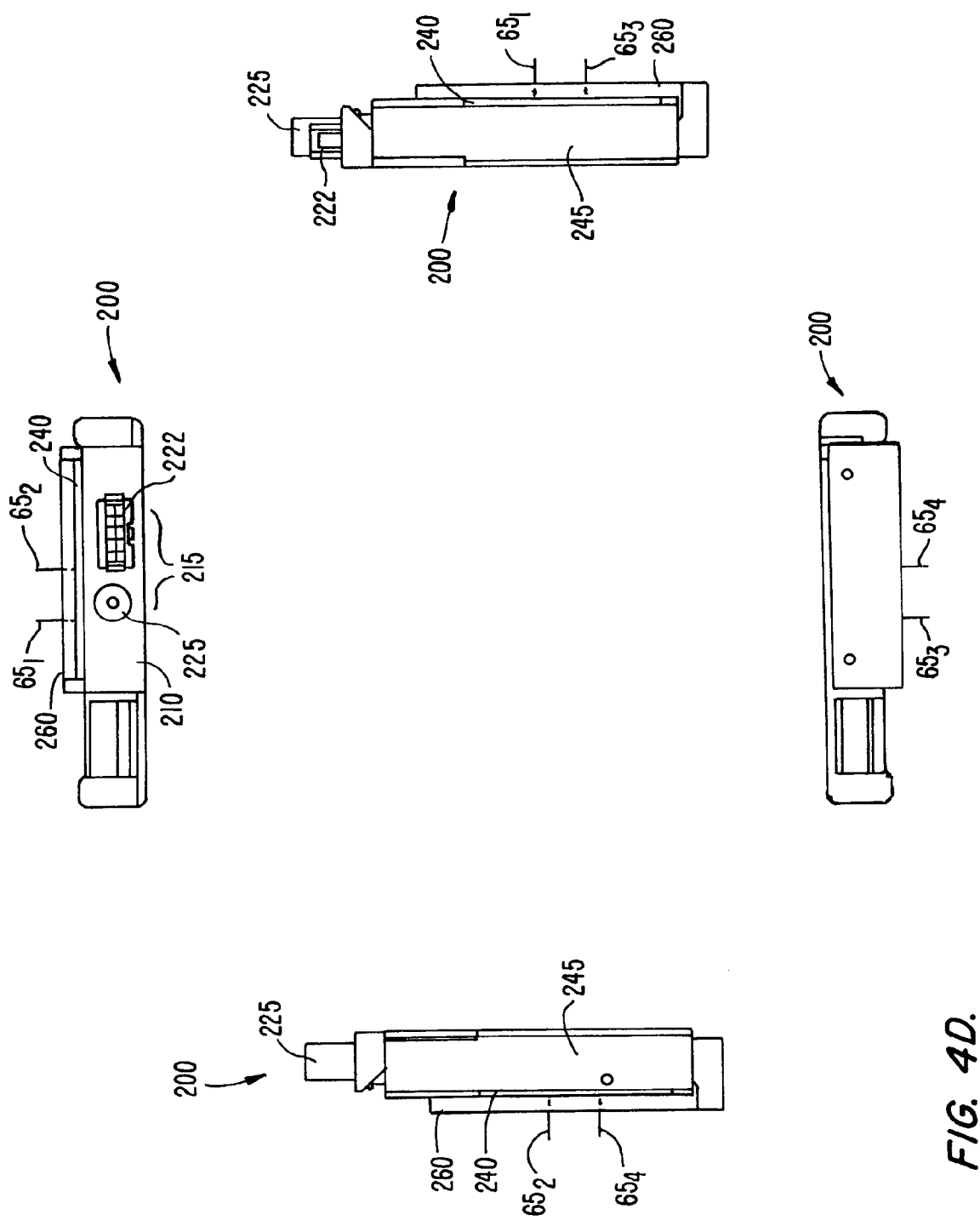

FIG. 4d illustrates side views of an exemplary modular interface structure 200 according to an embodiment of the present invention. As shown in FIG. 4d, interface structure 200 is in an "attached" state, i.e., each module is removably attached to the next, and the holder module 220 is removably attached to the sample substrate 240. A frame 245 is optionally provided as a structure for holding the modular interface structure. For example, one or more of the interface modules can be provided with locating pins or holes for mating with locating holes or pins 250 of frame 245. Alternately, adapter module 210, or any other module, may act as a frame structure. Sample substrate 240 as shown is a chip including a connection to four sampling capillaries $65_{1-4}$ (each side view only shows two of the capillaries). As will be described later, optional heater block module 260 is provided for heating and cooling fluid wells and reservoirs and reaction channels.

Figure 5B:
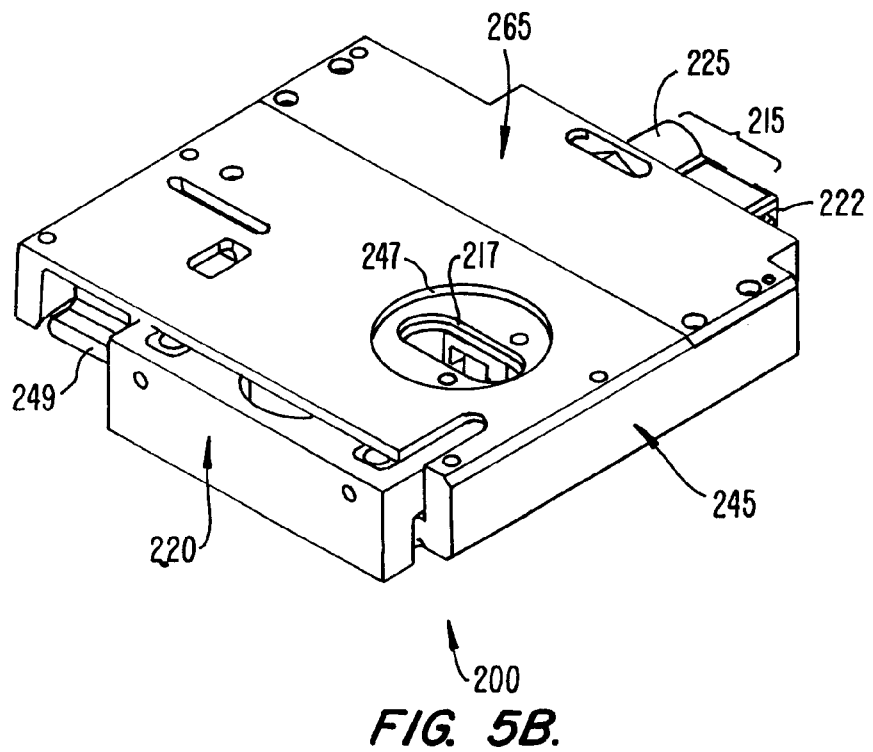

FIG. 5a illustrates an isometric view of the exemplary modular interface structure 200 of FIG. 4 including a frame structure 245 according to an embodiment of the present invention. As illustrated, optional frame 245 includes a window or opening 247 defined therein to allow radiation to pass therethrough, such that when attached to structure 200, window or opening 217 of adapter 210 is adjacent to the window or opening 247 of frame 245. Any additional modules in the interface structure 200 positioned between adapter module 210 and substrate 240 (e.g., a fluid supply module) include a window or opening defined therein to allow radiation to pass to and from the detection region on the substrate 240. A separate connection bracket 265 is optionally provided to add connectivity functionality for the overall interface structure. Connection bracket 265 includes locating pins and/or holes for mating with locating holes and/or pins of frame 245 and/or the various modules. Also included are guide portions 252 for mating with corresponding portions 252' on holding module 220. For example, as shown, guide portion 252 is a ledge for slidably receiving a corresponding ledge on holder module 220. Also shown is release lever 249 in the "open" position. FIG. 5b illustrates an isometric view of the exemplary modular structure of FIG. 5a in an "attached" state according to an embodiment of the present invention. Release lever 249, as shown, is in the "closed" position.

Locations and Patterns of Sampling Capillaries

As discussed above, sampling capillaries bring compounds onto chips from an external source. In current practices used by the pharmaceutical industry, desired compounds are primarily stored in microtiter plate formats, typically having 96 wells, 384 wells, or 1536 wells, and having well center spacings of 9 mm, 4.5 mm and 2.25 mm. Thus, in one embodiment, the spacing pattern of sampling capillary connection regions on chips, and therefore the spacing of any attached sampling capillaries, is preferably compatible with the microtiter plate spacing of 9 mm, 4.5 mm and/or 2.25 mm, although other spacings may be used as desired.

Figure 6:
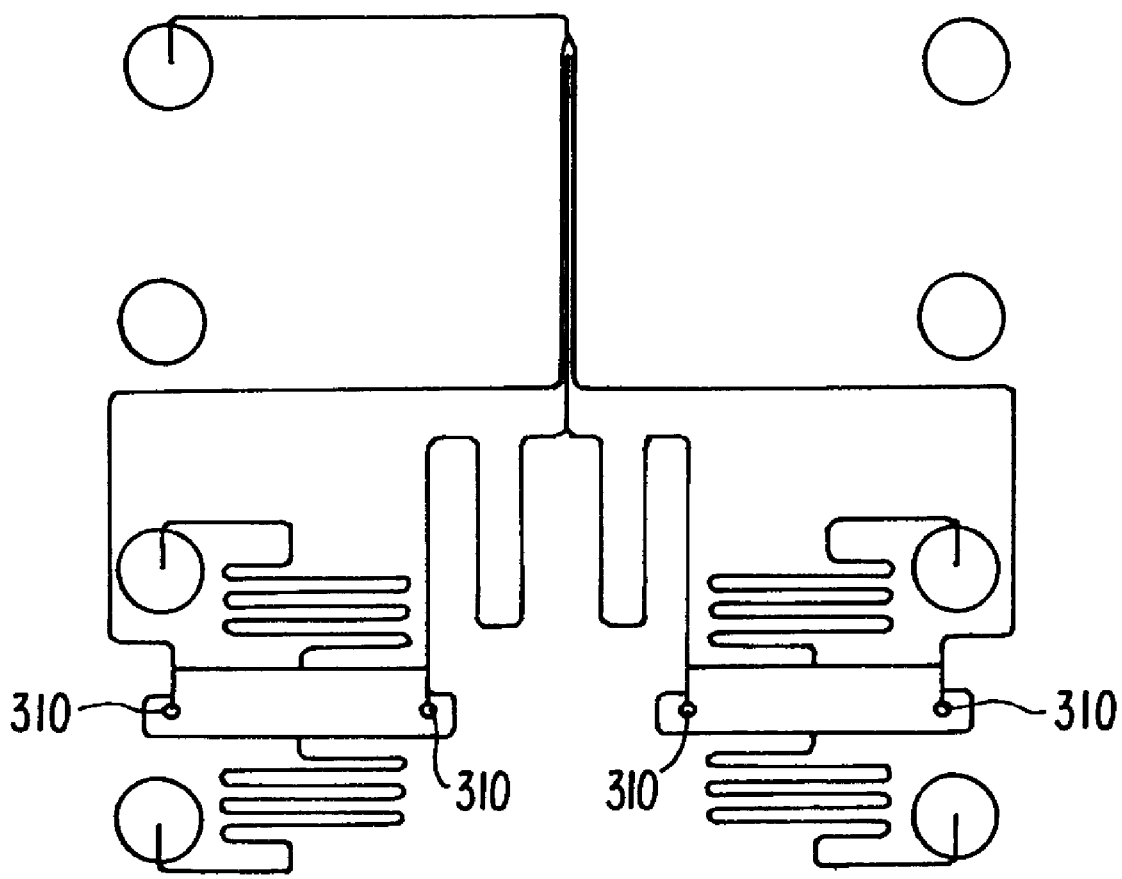
FIG. 6 illustrates a mask design with a spacing pattern for a linear array of four capillary connection regions that is compatible with typical microtiter plate format spacings according to one embodiment of the invention.

FIG. 6 illustrates a linear array of four capillary connection regions 310 on a microfluidic device 300 that is compatible with typical microtiter plate format spacings according to one embodiment of the invention. As shown, the capillary connection regions 310 are aligned linearly with an equal spacing between each. In one embodiment, the spacing between each connection region 310 is approximately 9 mm. When such a linear array is extended to 12 capillary connection regions, the dimension of the device becomes very large, and the outer channels became very long when channels are necked down into the middle for detection. Such qualities are generally undesirable in such microfluidic devices. In general, therefore, an optimal spacing arrangement of an array of capillary connection regions on a microfluidic device should satisfy some or all of the following criteria:

1. Maintain spacing compatible with microtiter plate formats;
2. Sample all compounds on the microtiter plate with only a single visit from the capillaries for each well;
3. Minimize the need for very long channels connecting to some of the capillaries;
4. Minimize substrate (wafer) usage per chip;
5. Allow adequate spacing for on-chip reagent wells to provide easy reagent delivery to all channels;
6. Provide a common spacing format to allow for scaling up the number of capillaries with minimal or no redesign; and
7. Design spacing patterns so that patterns of a smaller number of sampling capillaries are perfect subsets of a pattern of a larger number of capillaries so that channel redesign is minimal in scaling, e.g., from 12 capillaries to 4 capillaries to 1 capillary.

Figures 7A, 7B:
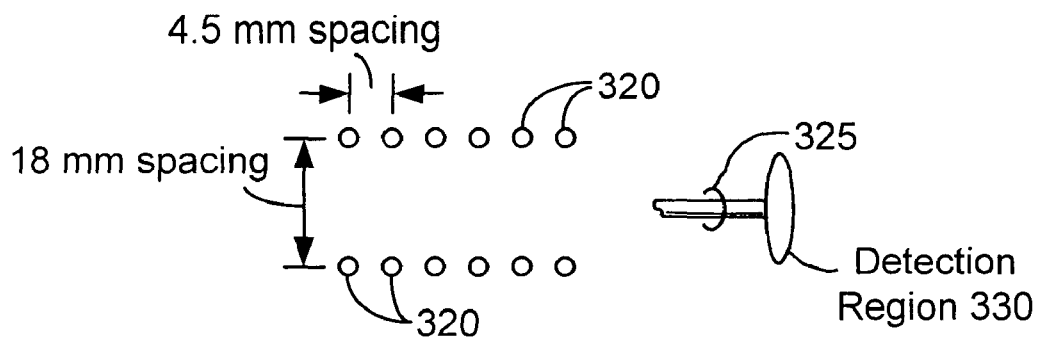

FIG. 7a illustrates a capillary spacing pattern according to one embodiment which satisfies all of the above design criteria. The pattern shown is compatible with both 96-well microtiter plates for chips having up to 6 sampling capillaries and with 384-well microtiter plates for chips having any number of sampling capillaries as shown in FIG. 7b. In a preferred embodiment, a non-linear array of capillary connection regions 320 is provided as shown, where the spacing between capillary connection regions 320 along a first direction defined by the plurality of microchannels 325 entering the detection region 330 are equally spaced so as to be compatible with microtiter plate format spacings. For example, in one embodiment as shown, two parallel linear arrays (altogether a non-linear array) of capillary connection regions 320 are provided with the spacing along the first direction being approximately 4.5 mm apart and the spacing of the two linear arrays being approximately 18 mm apart. This spacing pattern shown also fits into a 57×57 mm diced quartz or glass chip, which maximizes the use of 5" square wafers with 4 chips per wafer as shown in FIG. 2.

FIG. 7b illustrates various capillary placement patterns associated with the spacing pattern of FIG. 7a where the number of attached sampling capillaries is displayed to the left of each pattern.

In some embodiments, it may be necessary to rotate the orientation of the chip relative to the microtiter plate by 90 degrees to provide proper accession (i.e., visiting all wells with each well only visited once). For example, for the six capillary spacing pattern of FIG. 7b, it may be necessary to rotate by 90 degrees the orientation of the chip relative to the microtiter plate to provide proper accession for a 96 well microtiter format. It will be apparent that either the plate or the chip can be rotated while keeping the other fixed, although rotating both the chip and the plate to provide the 90 degree rotation is also possible.

Figure 8A:
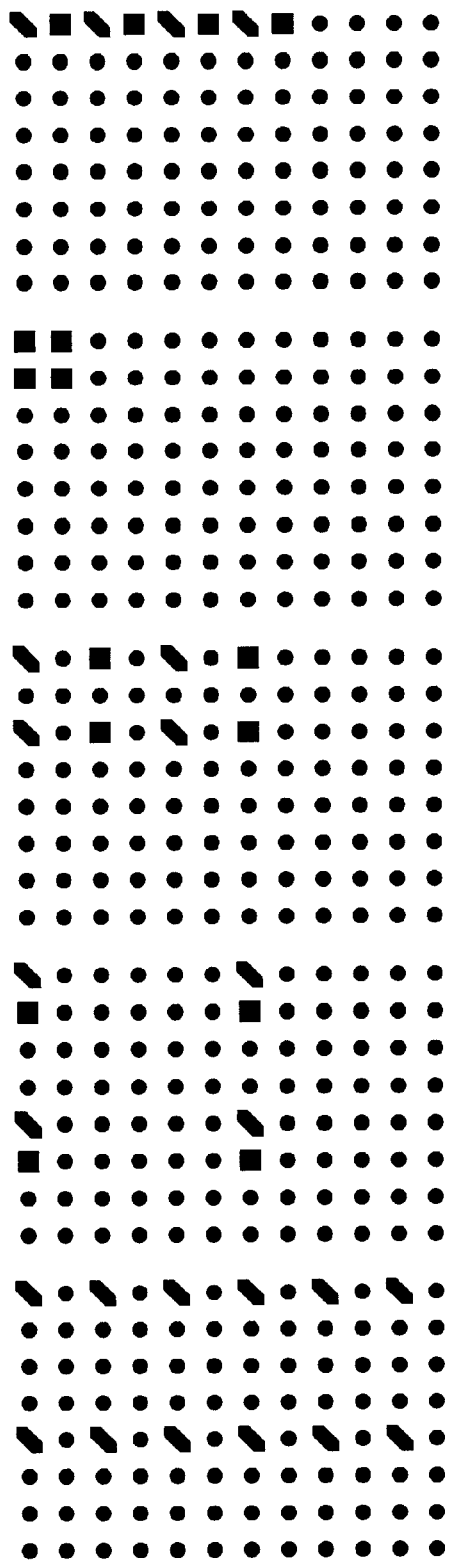
FIGS. 8a–b illustrate various capillary placement patterns according to an embodiment of the present invention.
Figure 8A:
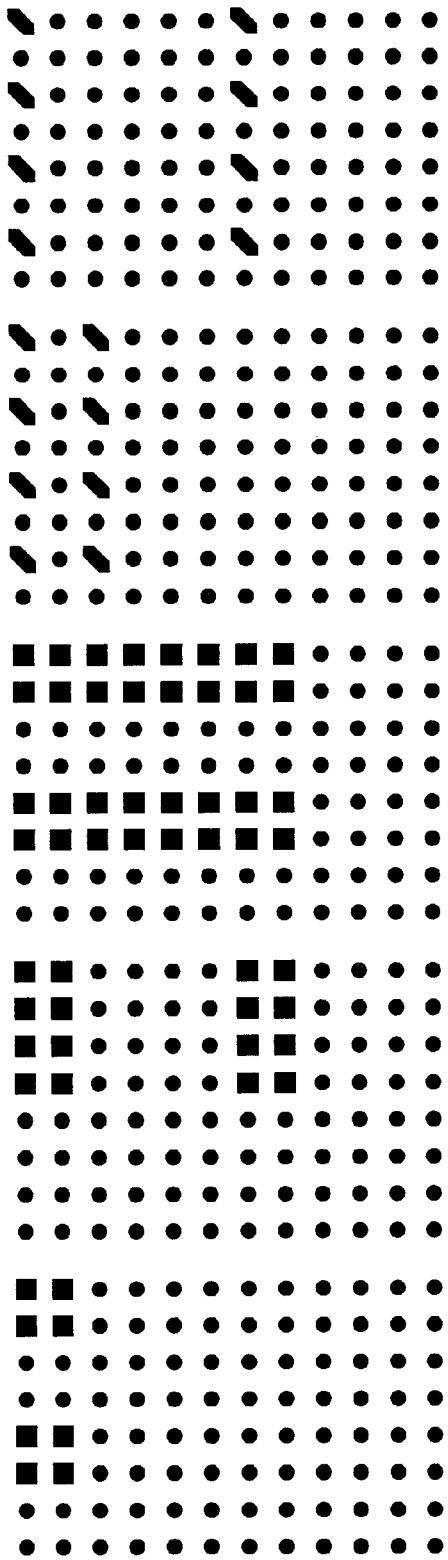
Figure 8B:
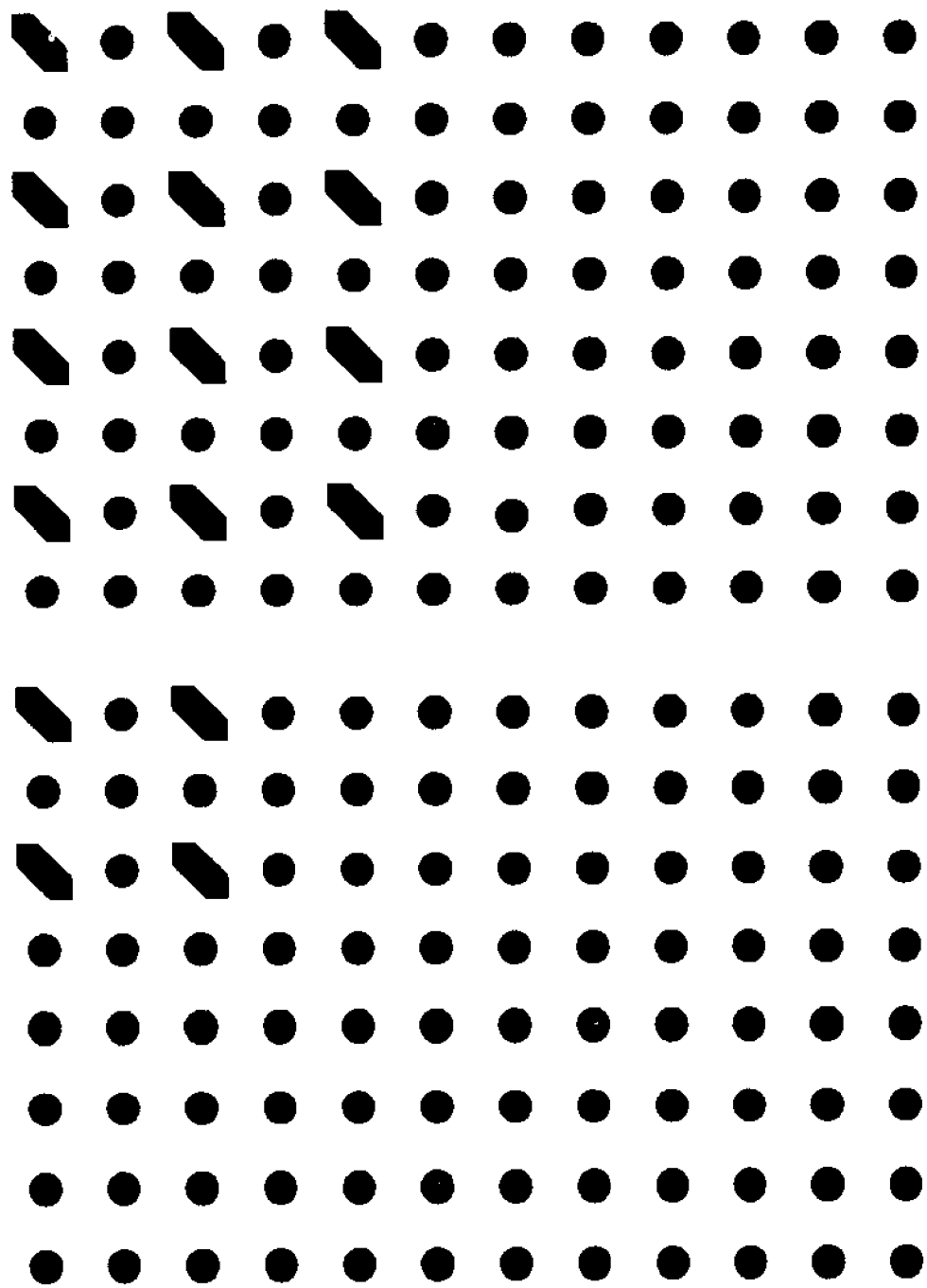

FIGS. 8a–b illustrate various capillary placement patterns according to another embodiment of the present invention. In the placement patterns shown, the spacing of the capillary connection regions are preferably compatible with microtiter plate format spacings as described above.

Although sampling capillaries are often comprised of capillaries attached to the body structure, in some cases the sampling capillaries will comprise mere extensions of the body structure, e.g., from a side or surface of the body structure. Such an extension would include a channel to the exterior of the device for sampling materials.

Number, Locations and Sizes of Reagent and Buffer Wells

Figure 9:
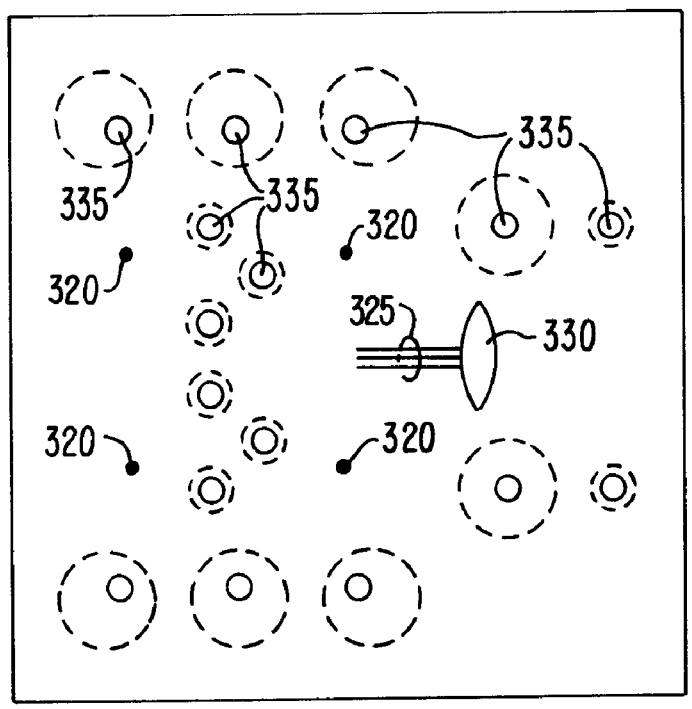
FIGS. 9 and 10 illustrate sampling capillary patterns for a 16-well format for 4 capillaries and a 30-well format for 12 capillaries, respectively, according to one embodiment.
Figure 10:
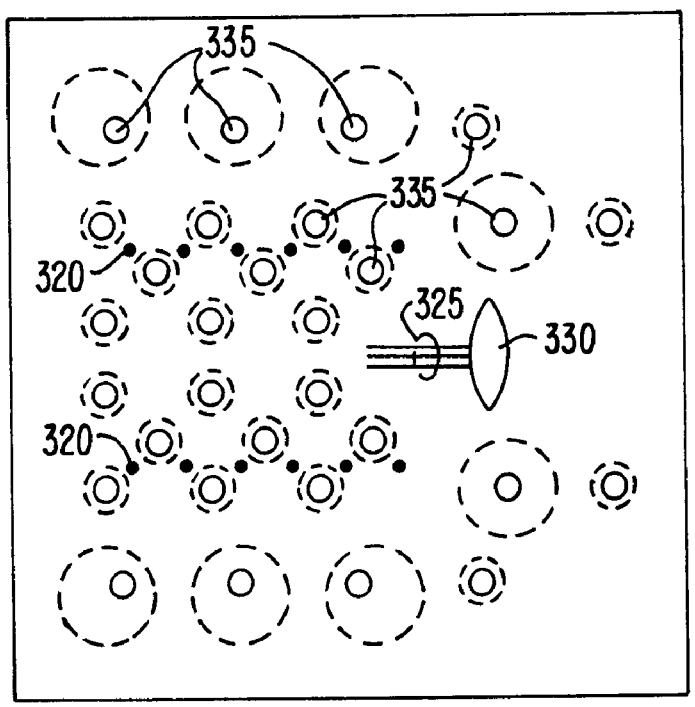

Due to topological constraints of the two-dimensional micromachined channel networks, on-chip reagent wells can usually only be shared between two parallel channel networks. Consequently, the minimum number of reagent wells required increases with the number of sampling capillary connection regions provided on a chip. It is therefore desirable to provide a common reagent well format in holder module 120 to allow flexibility in the selection of assay formats and in the selection of the number of attached sampling capillaries such that it is easy to scale up multiple sampling capillary compatible microchips. One consideration of a common format is that for most assays it is advantageous that the entry points for on-chip reagents and buffers into a reaction channel be located near a capillary-to-channel junction, i.e., sampling capillary connection region 40, to minimize compound dispersion due to flow and thermal diffusion. Another consideration is the volume requirement for extended operations, such as 8 continuous hours of operation per day. For example, the buffer flow rate for DMSO dilution is generally much higher than the enzyme and substrate flow rates in an enzymatic assay. With these considerations in mind, many different well formats with different sampling capillary connection region locations can be designed for use with any number of sampling capillaries. For example, FIG. 9 illustrates a format including 16 wells 335 and a non-linear array of 4 sampling capillary connection regions 320 for use with up to 4 sampling capillaries according to one embodiment of the present invention. FIG. 10 illustrates a format including 30 wells 335 and a non-linear array of 12 sampling capillary connection regions 320 for use with up to 12 sampling capillaries according to one embodiment of the present invention.

Heating and Cooling of Reagents and Channels

Figure 11:
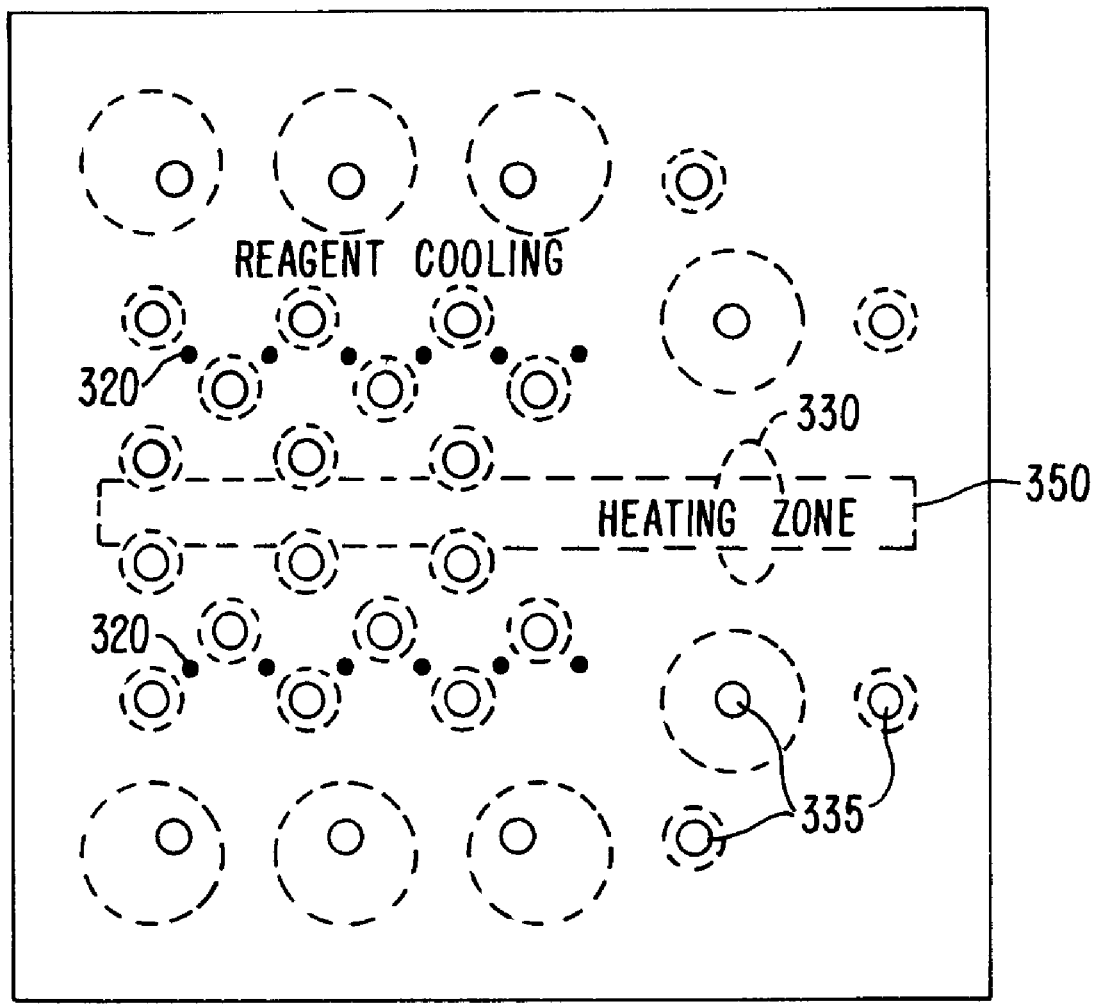
FIG. 11 illustrates a thermoelectric temperature control unit and a heater block for controlling temperatures according to one embodiment of the present invention.

In a multiple sampling capillary format (i.e., including more than one sampling capillary connected to the substrate), it is generally desirable to provide reagent cooling in some or all wells to slow down degradation during an extended period of operation. It is also desirable to provide reaction mixture heating in some channels, and particularly in the two or more channels entering the detection region of the substrate, to speed up the rates of reactions. According to one embodiment, a thermoelectric temperature control interface is optionally provided to control temperatures in the wells, and a heater module (e.g., heater module 160 of FIG. 3) is optionally positioned below the chip along the reaction channels for heating the reaction channels, which in one embodiment generally run parallel within heating zone 350 as shown in FIG. 11. In one embodiment, the thermoelectric temperature control interface includes "cold fingers," e.g. pins or electrodes or any other type of connector that provides for heat transfer, that dip into one or more reagent wells to reduce the temperature of reagents in the wells as desired. The transition zones between the cooled and heated regions will generally assume a temperature gradient depending on the thermal properties of the materials being used for the holder layer and the substrate. Examples of desired materials include plastics and polymers such as polymethylmethacrylate (PMMA), polycarbonate, polytetrafluoroethylene (TEFLON™), polyvinylchloride (PVC), polydimethysiloxane (PDMS), polysulfone, polystyrene, polymethylpentene, polypropylene, polyethylene, polyvinylidine fluoride, ABS (acrylonitrile-butadiene-styrene copolymer), and the like for the holder layer and glass or quartz for the substrate. In general, the temperature range of the extreme using these desired materials will be relatively small (for example, from 4° C. to 30° C.) so that local thermal expansion should not cause problems such as delamination of a holder from a quartz chip.

Automatic Refilling of Fluid Reservoirs

Figure 12A:
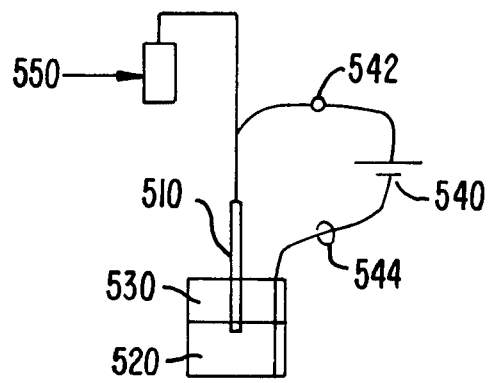
FIGS. 12a, b and c illustrate a simple circuit used to control the replenishment of fluid within the reservoir according to an embodiment of the present invention.
Figure 12B:
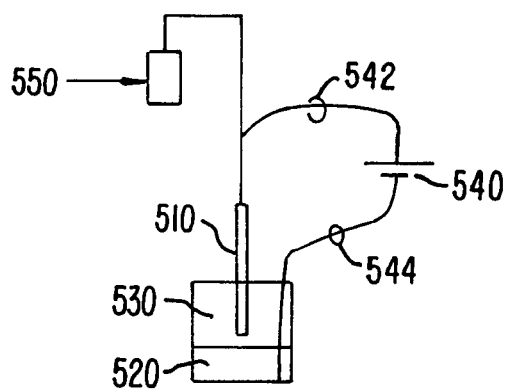
Figure 12C:
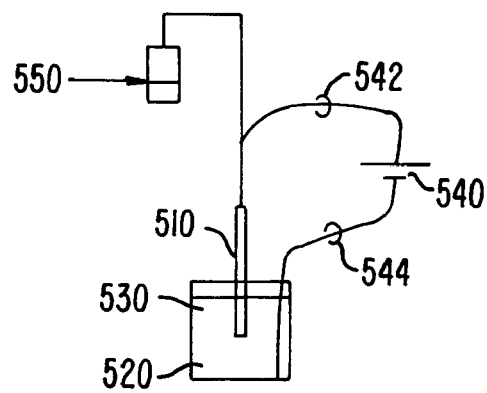

According to one embodiment, the electrical conductivity of the fluid within a reservoir is used to control the replenishment of fluid within the reservoir. FIG. 12a illustrates a simple circuit constructed from a conducting capillary 510, a conducting fluid 520 within a fluid reservoir 530, a voltage source 540, and two electrical leads 542 and 544. Examples of fluids having conducting properties include aqueous buffers with dissolved ionic species, such as salt solutions, assay buffers, and water. Examples of such assay buffers include CAPS (3 cyclohexylamino-1-propane sulfonic acid), TRIS (tris hydroxymethyl amino methane), PBS and HEPES. In general, any fluids with ionic species will have conducting properties, depending on the concentration of the ionic species. As shown, lead 542 originating from the positive terminal of voltage source 540 is connected to capillary 510, one end of which is initially immersed in conducting fluid 520. Lead 544, connected to the negative terminal of voltage source 540, is also placed in reservoir 530, but to a level slightly below that of capillary 510. It will be apparent to one skilled in the art that the polarity of voltage supply 540 as shown can be reversed without affecting the operation of the circuit. In operation, application of a voltage allows current to pass from the positive terminal, through capillary 510, through conducting fluid 520 and back to the negative terminal of voltage source 540. As the fluid 520 is consumed by the microfluidic device, the liquid level inside reservoir 530 drops until capillary 510 is no longer in contact with conducting fluid 520. This situation is illustrated in FIG. 12b. The resulting open circuit triggers a dispense of fluid through capillary 510 to reservoir 530 using an appropriate fluid metering device 550, such as a syringe pump or other device capable of providing fluid from a reservoir of fluid. For example, in one embodiment, the open circuit triggers a fixed volume dispense of fluid from a second reservoir using fluid metering device 550. FIG. 12c illustrates an example of the level of fluid 520 in reservoir 530 after fluid has been dispensed from a second reservoir using metering device 550 (as shown in FIGS. 12a–c, the second reservoir is integrated with metering device 550). This process is repeated each time the fluid level falls below the capillary, and may be operated continuously without user intervention. In an alternate embodiment, any low (e.g., non-zero) voltage level can be used to trigger the fluid refill dispense.

For example, in one embodiment, referring to FIG. 3, this technique is used to refill one or more reservoirs in holder layer 120 with fluid from one or more separate fluid reservoirs in fluid layer 130. In this embodiment, leads 542 and 544 can be implemented as electrodes or other electrical connectors in the interface modules, capillary 510 can be implemented as a capillary or any other type of fluid connector, and voltage source 540 can be provided in any of the modules or as an external voltage source.

In an alternate embodiment, a non-conducting capillary can be used for fluid refill. In this embodiment, automatic refill is triggered using two electrodes (each coupled to different terminals of voltage supply 540) positioned at different locations within the reservoir. In yet another embodiment, one of the electrodes can be positioned in a second reservoir in fluid communication with the first reservoir, which is refilled by the non-conducting capillary.

Illumination and Detection System

According to one embodiment of the present invention, an illumination and detection system is provided for simultaneously exciting multiple samples with multiple wavelengths and for simultaneously detecting emissions of multiple wavelengths. For example, the illumination and detection system of the present invention is useful for a variety of optical analytic assays and applications using the various microfluidic devices and systems (e.g., device 10 of FIG. 1) described herein. Such analytical assays and applications include fluorescence detection assays, fluorogenic assay enzyme inhibition applications, fluorescence polarization assays, genetic screening assays, DNA sequencing by measuring the lifetime of fluorescent labels, etc.

Figure 13:
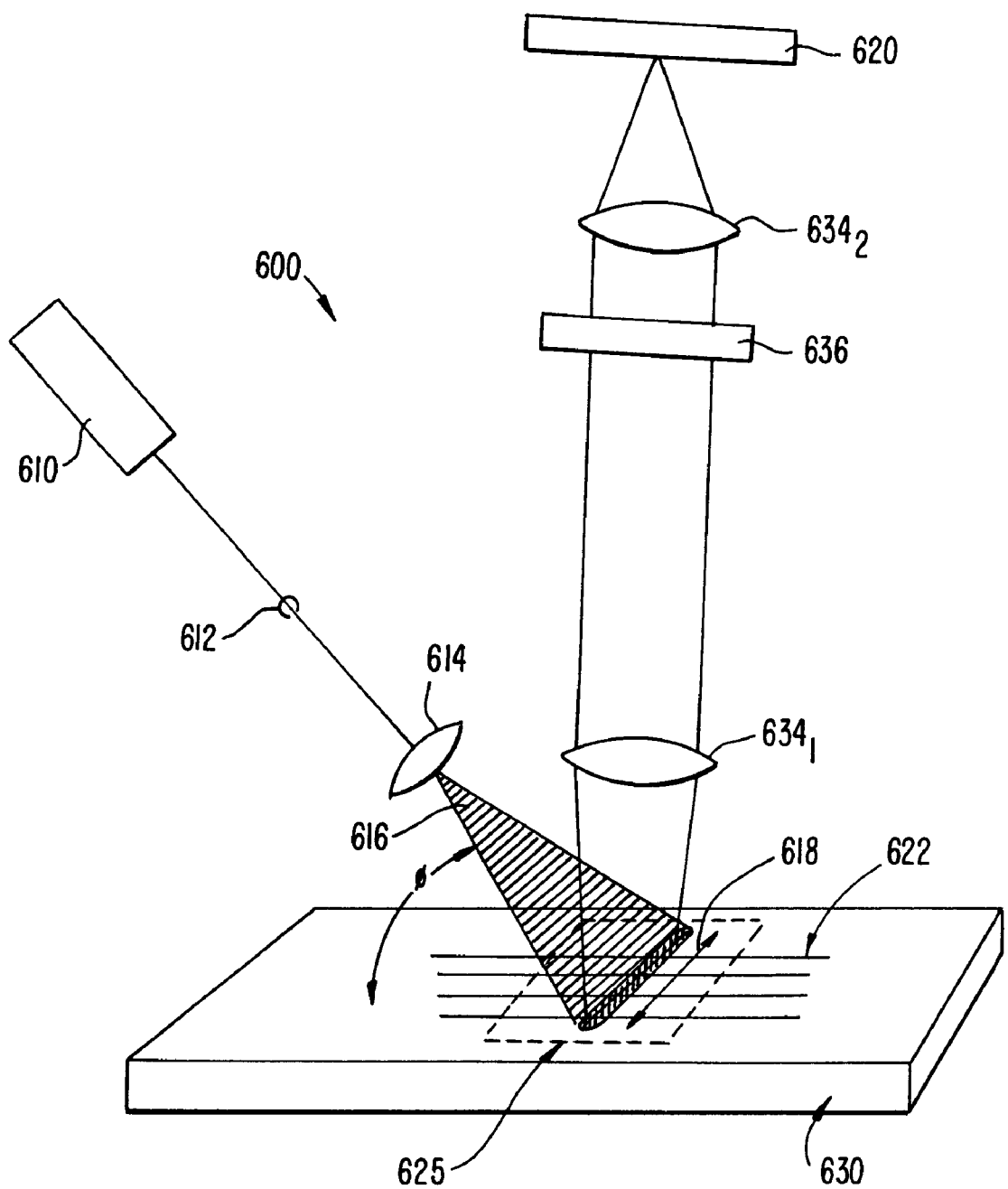
FIG. 13 illustrates an illumination and detection system according to an embodiment of the present invention.

FIG. 13 illustrates an illumination and detection system 600 according to an embodiment of the present invention. Illumination and detection system 600 includes an excitation source 610 and a detector array 620 including one or more optical detectors such as CCD arrays. Excitation source 610 provides an excitation beam 612, which is optically focussed and controlled by one or more optical elements 614 (only one optical element is shown). In a preferred embodiment, optical elements 614 include one or more lenses, such as plano-convex lenses and plano-cylindrical lenses, that focus excitation beam 612 into a large aspect ratio elliptical illumination beam 616 as shown. Optical elements 614 are positioned and arranged such that elliptical spot 616 is focused to the detection region 625 on the sample substrate 630. Preferably, source 610 and/or optical elements 614 are positioned such that elliptical excitation beam 616 impinges on substrate 630 at a non-normal angle of incidence, φ. In a preferred embodiment, φ is approximately 45 degrees relative to the plane defined by substrate 630, although other non-normal angles of incidence may be used, e.g., from about 30 degrees to about 60 degrees. In one embodiment, source 610 and optical elements 614 are arranged such that elliptical excitation beam 616 is polarized with a polarization direction/vector 618 that is substantially parallel to the major axis of elliptical excitation beam 616. Optical elements 614 are also preferably arranged such that the major axis of the resulting elliptical excitation beam 616 is substantially perpendicular to the direction of the microchannels 622 in detection region 625 as shown. Alternatively, the major axis of the elliptical excitation beam spot is oriented along the length of one or more of the microchannels 622 in detection region 625, in order to excite and detect a longer region of each of the channels, e.g., where a time dependent reaction is being monitored, or where detection sensitivity requires extended detection. In this manner, substances in each of the microfluidic channels 622 may be simultaneously excited by elliptical excitation beam 616. Emissions emanating from the samples in each of the plurality of microchannels 622 in detection region 625 are focussed and/or directed by one or more optical elements 634 (two element shown) onto detector array 620. At least one optical element, e.g., element $634_1$, such as an objective lens, is preferably positioned to direct emissions received from detection region 625 in a direction normal to the plane defined by the chip 630 as shown. One or more band-pass filter elements 636 are provided to help prevent undesired wavelengths from reaching detector array 620. A more detailed description of the various elements of illumination and detection system 600 will be presented with reference to FIGS. 14 and 15 below.

Figure 14:
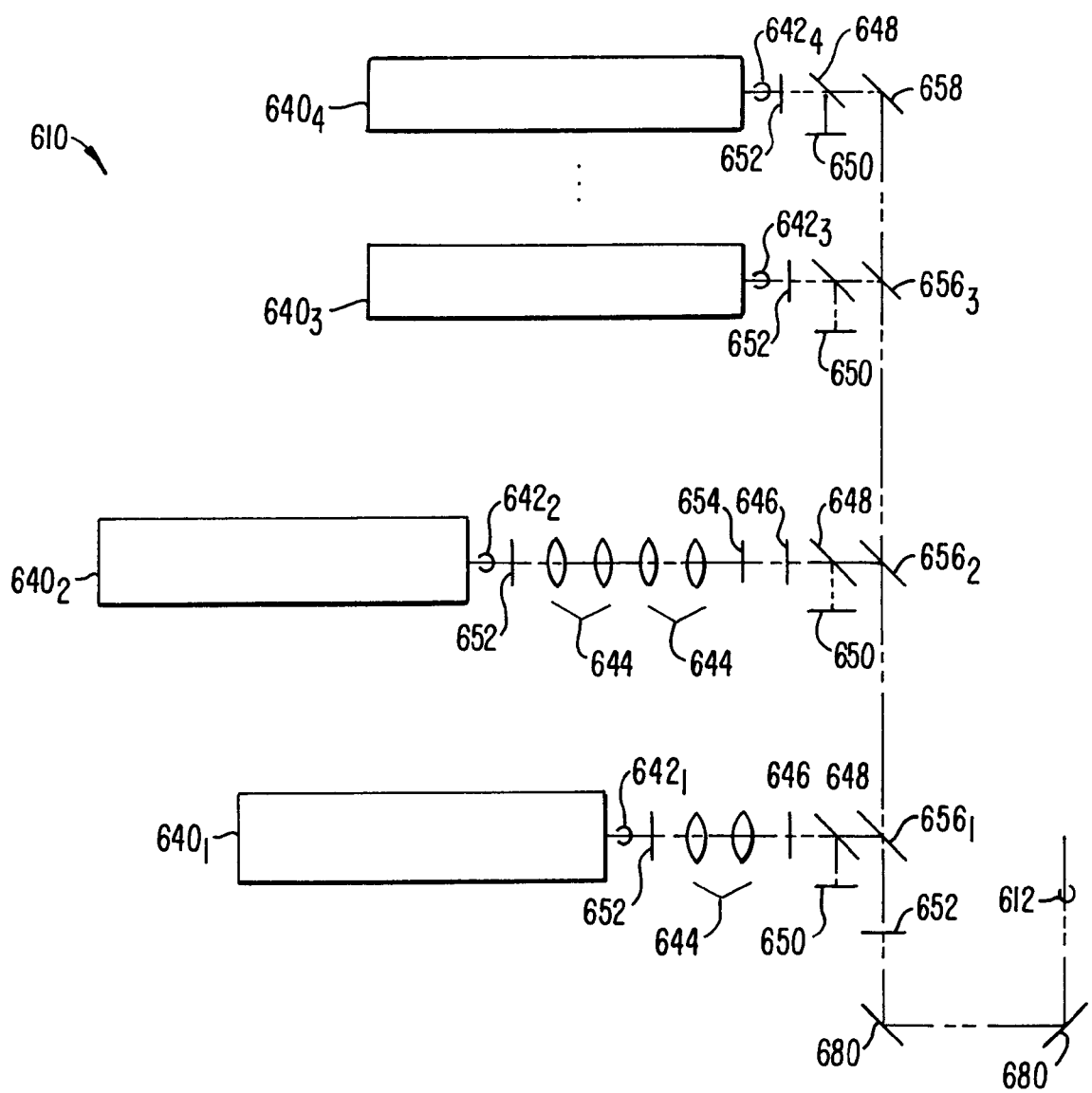
FIG. 14 illustrates details of an excitation source for providing an excitation beam for exciting samples in a plurality of microchannels according to an embodiment of the present invention.

FIG. 14 illustrates details of an excitation source 610 according to an embodiment of the present invention. In a preferred embodiment, excitation source 610 includes two or more optical radiation sources, each of which emits a radiation beam at a specific wavelength. For example, as shown in FIG. 14, excitation source 610 includes four laser sources $640_{1-4}$, each outputting a radiation beam $642$ having at least one defined wavelength. Output beams $642_{1-4}$ from lasers $640_{1-4}$ are combined through the use of various beamsplitter elements and other optical elements to create excitation beam 612. In one embodiment, telescopes 644 of various magnifications are used to expand some or all of beams $642_{1-4}$ so as to equalize the geometries of output beams $642_{1-4}$. Filters 646, such as neutral density filter wheels, are also provided to equalize the powers of output beams $642_{1-4}$. Beam samplers 648 and reference detectors 650 are optionally provided to monitor power levels and to permit subsequent signal normalization, e.g., fluorescence signal normalization. In the embodiment as shown in FIG. 14, only two output beams $642_1$ and $642_2$ require the use of telescopes and filters. However, it will be apparent that none, some or all beams 642 may require expansion and filtering to equalize powers and geometries depending on the particular radiation source used. Shutters 652 are optionally provided to allow the capability to cut off the respective beam 642, as well as beam 641, when not required for the specific application or assay. A half wave retarder, or other polarization altering element, is optionally provided for each output beam 642 to provide polarization adjustment capability as needed.

Mirror element 658, which in one embodiment is a dielectric mirror, is optionally provided and positioned to reflect beam $642_4$ toward beamsplitter elements 656. Laser source $640_4$ may be positioned such that output beam $642_4$ is directed toward beamsplitter elements 656. Beamsplitter elements 656 are provided and positioned to combine output beams 642. For example, as shown, beamsplitter element $656_3$ combines beam $642_4$ with beam $642_3$. Beam element $656_3$ reflects at least a substantial portion of beam $642_3$ toward beamsplitter elements $656_2$ and $656_1$, and allows at least a substantial portion of reflected beam $642_4$ to pass through toward beamsplitter elements $656_2$ and $656_1$, such that the two beams are combined. In the same manner, beamsplitter elements $656_2$ and $656_1$ each reflect at least a substantial portion of beams $642_2$ and $642_1$, respectively, and each allows at least a substantial portion of the combined upstream beams to pass so as to ultimately produce excitation beam 612. In one embodiment, beamsplitter elements 656 are dichroic beamsplitters that are capable of reflecting the defined wavelength of the respective laser source 640 and that are capable of allowing the other defined wavelengths to pass, as are well known in the art. It will, of course, be apparent that other elements that provide such capabilities may be used, e.g., dichroic "cold" mirrors. Mirror elements 680 are optionally provided to direct excitation beam 612 toward focussing optics 614 (see FIGS. 13 and 15).

According to one embodiment, each laser source 640 is capable of outputting radiation having at least one primary wavelength. Examples of useful laser sources include HeNe lasers, Argon Ion lasers, tunable dye lasers, semiconductor lasers, free electron lasers, excimer lasers, etc. Different laser sources can be selected depending on the desired output wavelengths and power requirements. In general, it is desirable to provide at least two laser sources, each outputting a beam having a different wavelength in a range from about 300 nm (UV) to about 700 nm (red). For example, in a preferred embodiment, depending on the desired application, laser sources 640 are selected so that excitation beam 612 includes at least two or more of the following approximate wavelengths: 355 nm, 457 nm, 488 nm, 532 nm and 633 nm. For fluorescein excitation applications, or fluorescence polarization detection applications, for example, an Argon ion laser outputting a beam with a wavelength of approximately 488 nm is desirable.

Figure 15:
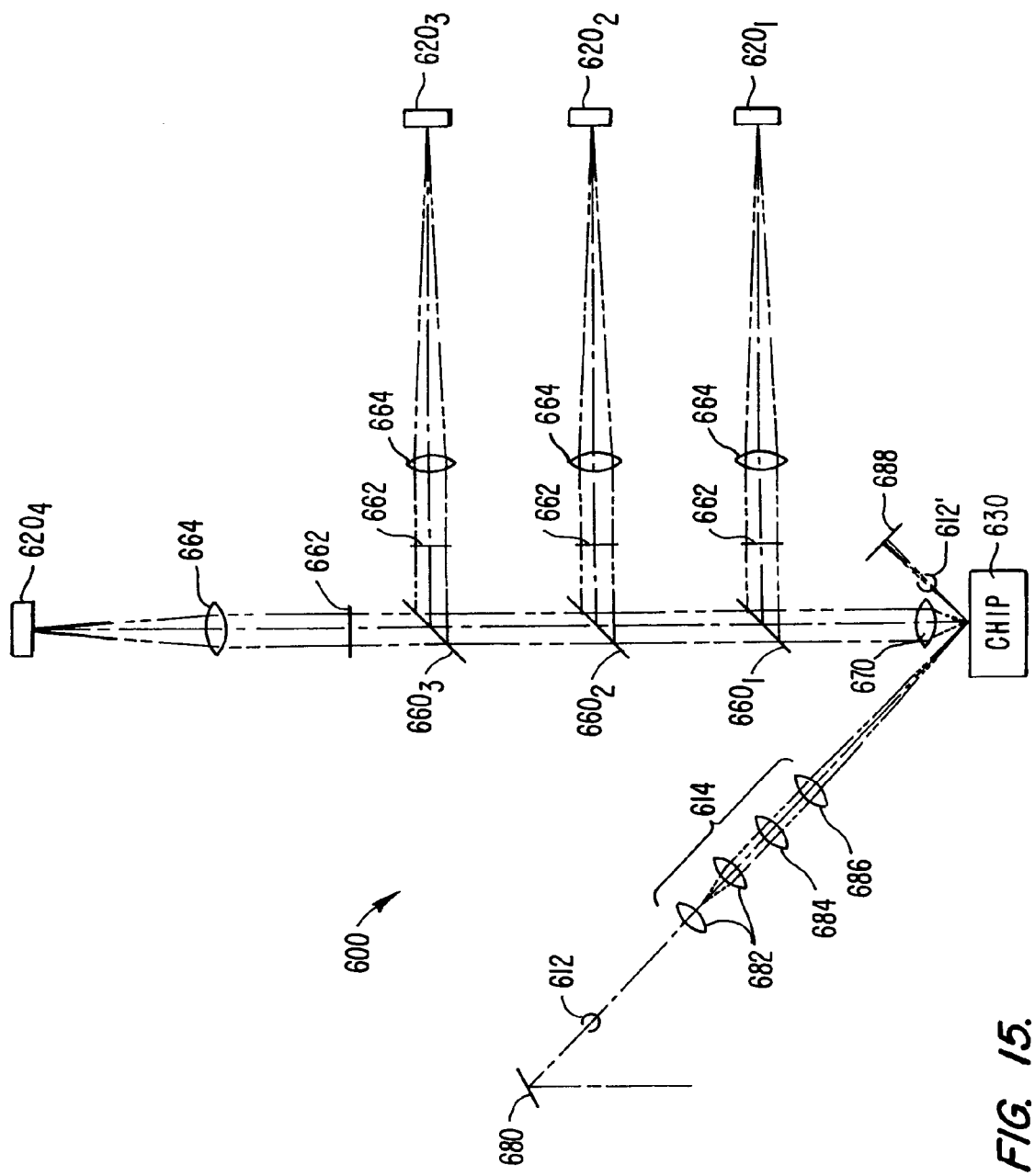
FIG. 15 illustrates various optical elements of an illumination and detection system in more detail according to an embodiment of the present invention.

FIG. 15 illustrates various optical elements of illumination and detection system 600 in more detail according to an embodiment of the present invention. In one embodiment, one or more mirror elements 680 are optionally provided and positioned to direct excitation beam 612 toward optical elements 614 in a desired direction. In a preferred embodiment, excitation source 610, or mirror elements 680, and optical elements 614 are positioned such that excitation beam 612 illuminates the excitation and detection region on chip 630 at an angle of incidence of approximately 45°, although other non-normal angles may be used. This illumination is also preferably s-polarized. Optical elements 614, in one embodiment, include a telescope 682 for magnifying, or expanding, excitation beam 641, and an arrangement of a plano-convex lens 684 and a plano-cylindrical lens 686 as shown. Plano-convex lens 684 and plano-cylindrical lens 686 act in concert to create and focus elliptical excitation beam 616 from expanded excitation beam 612. Elliptical excitation beam 616 is focused onto the detection region of chip 630 with an elliptical spot having the desired dimensions and orientation so as to excite samples in two or more microchannels 622 in detection region 625 simultaneously. For example, in one embodiment, where microchannels 622 in detection region 625 have a width of approximately 100 micrometers and are spaced approximately 100 micrometers apart (relative to the center of each adjacent channel), the $1/e^2$ dimensions of the elliptical excitation spot are approximately 50×1000 micrometers formed with numerical apertures (NA's) of 0.010 and 0.017, respectively. In the present embodiment, plano-convex lens 684 in conjunction with plano-cylindrical lens 686 form an anamorphic focusing doublet which is responsible for forming elliptical excitation beam 616. However, plano-convex lens 684 may be replaced by a custom broadband triplet for significant chromatic aberration correction, where this triplet is optimized for this application where the specific wavelength range, piano-cylindrical lens 686, chip 630 cover glass thickness, and non-normal angle of incidence are taken into account (e.g., modified version of U.S. Pat. No. 3,486,805, by K. Kobayashi), which will enhance the performance of the optics.

Chip 630 is preferably aligned such that, within detection region 625, microchannels 622 run parallel to the elliptical excitation spot's minor axis, and such that the chemistry flows in the same direction as the illumination flux. One advantage of illuminating the chip at a non-normal angle of incidence is that doing so effectively prevents zero order reflections at a normal incidence relative to the chip, i.e., zero order reflections 612' will typically reflect off chip 630 at the same relative angle, $\phi$, at which excitation beam 612 impinges on chip 630. In one embodiment, as shown, a zero order stop 688 is provided to prevent any zero order reflections 612' from interfering with other parts of the system. Additionally, one advantage of exciting samples in two or more microchannels simultaneously is that multi-channel detection can be performed without scanning a beam across the microchannels.

The emission, or collection, optics will be described with reference to one embodiment wherein emissions from detection region 625 include fluorescence emissions from two or more of microchannels 622. The collections optics includes a focussing element 670, which in one embodiment is an objective lens, such as a large working distance, modest NA, fluorescence microscope objective lens (OL). A large working distance is helpful in accommodating complex chip designs. In the present embodiment, objective lens 670 may be used in an afocal mode in combination with focusing lenses 664, e.g., piano-convex lenses, to image the fluorescing chip channels onto detector arrays 620, which in one embodiment are CCD arrays. Objective lens 670 in this embodiment may be manually focussed, or may be focussed by a computer system as will be described later. The various fluorescence wavelengths, in one embodiment, are separated through the use of dichroic beamsplitters 660 in combination with band-pass filters 662. These beamsplitters operate in a similar fashion as beamsplitter elements 656 as described with reference to FIG. 14. For example, each beamsplitter element 660 directs fluorescence emissions within a specific wavelength range toward it respective detector 620, and allows wavelengths outside that range to pass. As shown, four detector arrays are included, each of which is provided for detecting a specific wavelength range. It will be apparent, however, that fewer or more detector arrays, and associated beamsplitter and focussing elements, may be used depending on the number of different wavelengths to be detected. Additionally, in one embodiment, some or all of filters 662 are polarizing specific filters to allow detection of specific polarization.

According to one embodiment, there are at least as many detector arrays 620 as laser sources 640. For example, in an embodiment using a first laser source emitting radiation having a wavelength of approximately 355 nm, and a second laser source emitting radiation having a wavelength of approximately 457 nm, at least two detectors (and at least one beamsplitter element) are provided for detecting fluorescence emissions from excited samples in the detection region of a substrate of approximately 440 nm and 530 nm, respectively.

Control System

Figure 16:
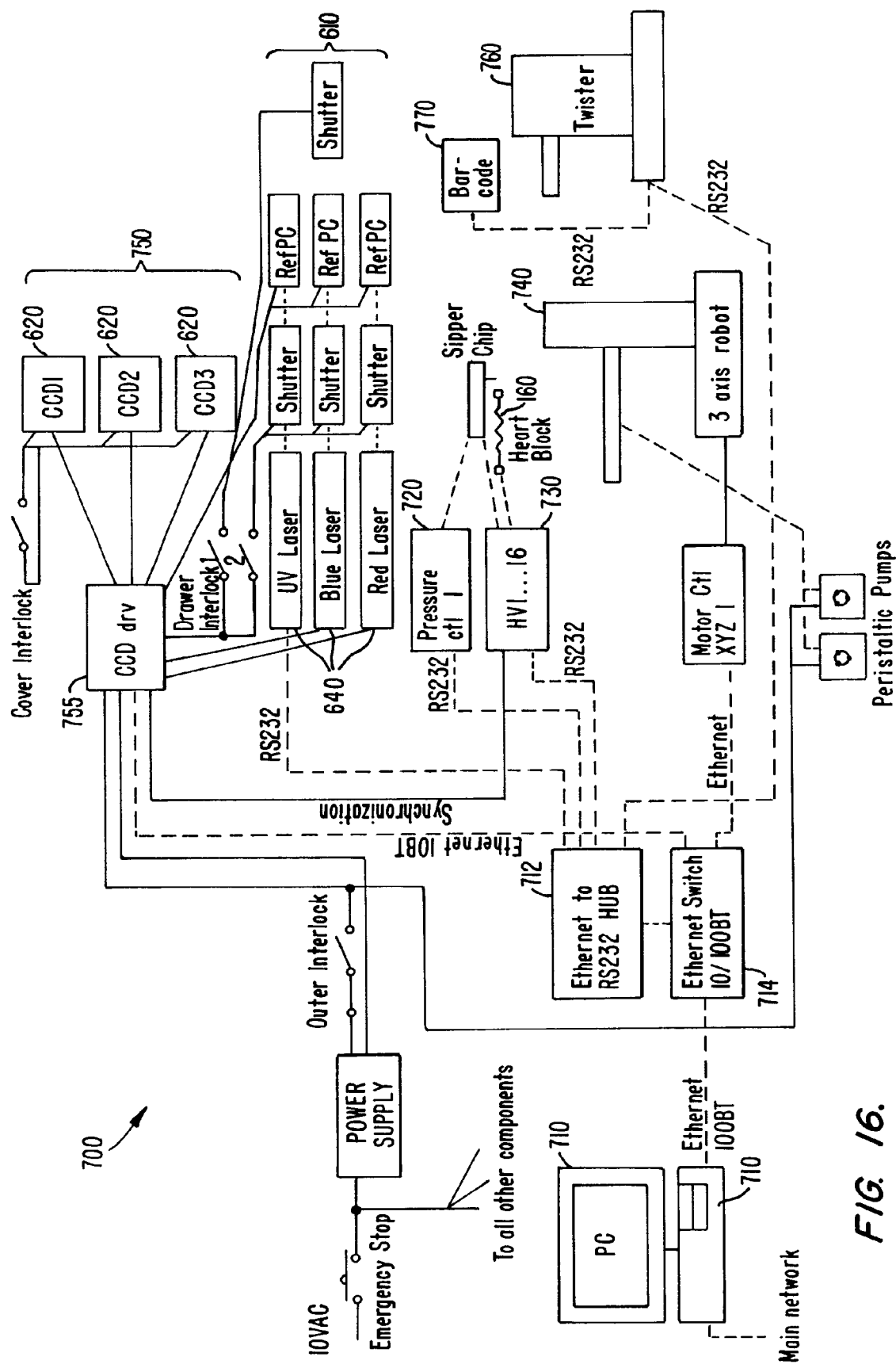
FIG. 16 is a block diagram illustrating the control system electronics according to an embodiment of the present invention.

FIG. 16 presents a block diagram of a control system 700 for configuring and operating the various systems, instrument interface array components, and modules referred to above. Control system 700 includes a host computer 710 that is preferably implemented as an industry standard Pentium-based personal computer executing the Microsoft Windows NT operating system, although any other processor and any other operating system may be used as desired. As part of its function, computer 710 coordinates the operation of all analytical systems, control systems and related components.

A local area network (LAN), based in one embodiment on Ethernet, is used to interface the various electronic modules that comprise the instrument, such as the CCD array modules 620, pump module 720, high voltage module 730, and a three-axes robot 740. Three axis robot 740 provides the capability to automatically place or replace microtiter plates, e.g., from a tray of microtiter plates, and interconnect them with the appropriate instrument interface array. Twister robot 760 is provided to place desired microtiter plates, e.g., from a tray of microtiter plates, to a specific area for access and placement by three-axis robot 740. Bar code reader 770 is provided to allow twister robot 760 to identify microtiter plates having bar code identifiers thereon. One or more Ethernet hubs or switches are provided to direct Ethernet protocol control signals to the desired modules to allow the various modules to be controlled. For example, in one embodiment, an Ethernet/RS232 converter 712 is configured to interface with high voltage module 730, pump module 720 and excitation module 610. In this embodiment, Ethernet switch 714 is configured to interface with detection module 750, which includes detector arrays 620 and theirs associated driver(s) 755. Host PC 710 in one embodiment is also connected to a main network. The host PC can configure and operate the entire instrument interface array through the use of custom control and data acquisition computer code/software. Such code is preferably stored on a hard disk coupled to computer 710, but may be stored on a server accessible by PC 710 over the main network. The entire program code, or portions thereof, may also be stored in any other memory device such as a ROM or RAM, or provided on any media capable of storing program code, such as a compact disk medium, a floppy disk, or the like.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of simultaneously analyzing a plurality of samples in a plurality of microchannels on a microfluidic device, wherein the plurality of microchannels are substantially parallel along a first direction within a detection region on the microfluidic device, the method comprising the steps of:

simultaneously exciting the samples in at least two of the microchannels in the detection region by focussing an excitation beam having two or more excitation wavelengths onto a first plane defined by the plurality of microchannels in the detection region such that the focussed excitation beam is elongated, having a major axis substantially perpendicular to the first direction, wherein the excitation beam impinges upon the detection region at a non-normal angle of incidence relative to the first plane, and wherein the excited samples emit radiation; and simultaneously detecting the radiation emitted by the two or more excited samples using two or more detectors, wherein each of the detectors detects a specific range of radiation wavelengths.

2. The method of claim 1, wherein the step of simultaneously detecting includes focussing the radiation emitted by the two or more excited samples toward a linear arrangement of beamsplitters, wherein each beamsplitter is associated with one of the detectors, and wherein each beamsplitter directs radiation within one of the specific ranges of wavelengths toward its associated detector.

3. The method of claim 1, further comprising the step of forming the excitation beam by combining the beams emitted from each of two or more laser sources, wherein each laser source emits a radiation beam having one of the excitation wavelengths.

4. The method of claim 1, further including the steps of:
providing an output signal from each detector to a processor, wherein each output signal is proportional to the radiation received from the detection region within each detector's specific range of wavelengths; and
analyzing the output signals in the processor.

5. The method of claim 1, wherein the microfluidic device includes at least two intersecting microchannels.

6. The method of claim 1, wherein each of the plurality of microchannels has at least one cross-sectional dimension between about 0.1 and about 500 micrometers.

7. The method of claim 1, wherein the microfluidic device includes a conducting capillary and a voltage supply, wherein a first end of the capillary is positioned at a first level within the reservoir, wherein a first terminal of the voltage supply is connected to the capillary and wherein a second terminal of the voltage supply is connected to a location at a second level within the reservoir, the second level being below the first level, the method further comprising the steps of:
detecting an absence of electric current between the first and second terminals through the capillary, wherein no electric current flows between the first and second terminals when the fluid level is below the first level in the reservoir; and
automatically supplying fluid to the reservoir through the capillary using a fluid monitoring device in response to the absence of current so as to raise the fluid level.

8. The method of claim 7, wherein the first terminal is positive and wherein the second terminal is negative.

9. The method of claim 7, wherein the step of automatically supplying fluid includes automatically supplying a predetermined amount of fluid.

10. The method of claim 1, wherein the microfluidic device includes:
a sample substrate having a plurality of substrate reservoirs and the plurality of microchannels disposed thereon, wherein the plurality of microchannels connects the plurality of substrate reservoirs, and wherein two or more of the microchannels are substantially parallel in the detection region on the substrate; and
a modular interface, having two or more removably attachable interface modules, for interfacing with a plurality of instrument connectors, the interface including:
a substrate interface module having at least one fluid reservoir disposed therein, wherein the substrate interface module is removably attached to the substrate, and wherein the at least one fluid reservoir is positioned so as to provide increased capacity to one of the substrate reservoirs; and
an instrument interface module having a plurality of first connectors for connecting to one or more of the plurality of instrument connectors, and a plurality of second connectors for providing a connection between the instrument connectors and the substrate interface module when the substrate interface module is removably attached to the instrument interface module.

11. The method of claim 1, wherein the microfluidic device is arranged on a sample substrate, and wherein the device includes:
a plurality of substrate reservoirs disposed on the substrate;
the plurality of microchannels disposed on the substrate, wherein the plurality of microchannels connects the plurality of substrate reservoirs, and wherein two or more of the microchannels are substantially parallel in the detection region on the substrate; and
a non-linear arrangement of a plurality of sampling capillary connection regions disposed on the substrate for interfacing with one or more sampling capillaries, wherein the sampling capillary connection regions are connected to the plurality of microchannels.

12. The method of claim 1, wherein the microfluidic device is arranged on a sample substrate, and wherein the device includes:
a plurality of substrate reservoirs disposed on the substrate;
the plurality of microchannels disposed on the substrate, wherein the plurality of microchannels connects the plurality of substrate reservoirs; and
two linear arrangements of two or more sampling capillary connection regions adisposed on the substrate for interfacing with one or more sampling capillaries, the sampling capillary connection regions being connected to the plurality of microchannels,
wherein for each linear arrangement, the sampling capillary connection regions are space approximately $n*2.25$ mm apart, where n is an integer having a value of from 1 to 24, inclusive.

13. A method of simultaneously analyzing a plurality of samples in a plurality of microchannels on a microfluidic device, wherein the plurality of microchannels are substantially parallel along a first direction within a detection region on the microfluidic device, the method comprising the steps of:
simultaneously exciting the samples in at least two of the microchannels in the detection region by focussing an excitation beam having two or more excitation wavelengths onto a first plane defined by the plurality of microchannels in the detection region such that the focussed excitation beam is elongated, having a major axis substantially perpendicular to the first direction, wherein the excitation beam impinges upon the detection region at a non-normal angle of incidence relative to the first plane, and wherein the excited samples emit radiation; and
simultaneously detecting the radiation emitted by the two or more excited samples using two or more detectors, wherein each of the detectors detects radiation having a specific polarization.

* * * * *

UNITED STATES PATENT AND TRADEMARK OFFICE
CERTIFICATE OF CORRECTION

PATENT NO.     : 6,547,941 B2
DATED          : April 15, 2003
INVENTOR(S)    : Kopf-Sill et al.

It is certified that error appears in the above-identified patent and that said Letters Patent is hereby corrected as shown below:

Column 22,
Line 36, please delete "adisposed" and insert -- disposed --.

Signed and Sealed this

First Day of July, 2003

JAMES E. ROGAN
*Director of the United States Patent and Trademark Office*